(12) United States Patent
Jentsch

(10) Patent No.: US 6,794,161 B1
(45) Date of Patent: Sep. 21, 2004

(54) POTASSIUM CHANNELS AND GENES ENCODING THESE POTASSIUM CHANNELS

(75) Inventor: Thomas J. Jentsch, Hamburg (DE)

(73) Assignee: NeuroSearch A/S, Bagsvaerd (DK)

( * ) Notice: Subject to any disclaimer, the term of this patent is extended or adjusted under 35 U.S.C. 154(b) by 0 days.

(21) Appl. No.: 09/492,361

(22) Filed: Jan. 27, 2000

Related U.S. Application Data

(60) Provisional application No. 60/118,112, filed on Feb. 1, 1999.

(30) Foreign Application Priority Data

Jan. 26, 1999 (DK) .......................................... 1999 00076
May 19, 1999 (DK) .......................................... 1999 00693

(51) Int. Cl.$^7$ ........................ C12N 15/12; C12N 15/63; C12N 15/00; C07K 14/00; C07H 21/04
(52) U.S. Cl. .................... 435/69.1; 435/320.1; 435/325; 530/350; 536/23.5
(58) Field of Search ............................. 435/69.1, 320.1, 435/325; 530/350; 536/23.5

(56) References Cited

U.S. PATENT DOCUMENTS 5,300,632 A * 4/1994 Murphy et al. ............. 530/420

FOREIGN PATENT DOCUMENTS

WO     WO 9401548 A2 * 1/1994

OTHER PUBLICATIONS

Eck & Wilson in Goodman & Gilman's The Pharmacological Basis of Therapeutincs, ninth Edition, McGraw Hill, New York, 199 pp. 77–101.*

Bowie et al. Deciphering the message in protein sequences: Tolerance to amino acid substitutions. 1990. Science vol. 247, pp. 1306–1310.*

Mikayama T. Molecular cloning and functional expression of a cDNA encoding glycosylation–inhibiting factor. Proc. Natl. Acad Sci. USA vol. 90, pp. 10056–10060, 1993.*

Voet et al. Biochemistry. 1990. John Wiley & Sons, Inc.. pp. 126–128 and 228–234.*

Eck & Wilson in Goodman's and Gilman's Pharmacological Basis of Therapeutincs. Ninth Edition. McGraw–Hill. New York 1996. pp. 77–101.*

"Genes responsible for human hereditary deafness: symphony of a thousand", C. Pritt, Nature Genetics, vol. 14, Dec. 1996 pp. 385–391.

"The fundamental and medical impacts of recent progress in research on hereditary hearing loss", V. Kalatzis et al., Human Molecular Genetics, 1998 vol. 7, No. 10 pp. 1589–1597.

"Positional cloning of a novel postassium channel gene: KVLQT1 mutations cause cardiac arrhythmias" Q. Wang et al., Nature Genetics, vol. 12, Jan. 1996 pp. 17–23.

"A Potassium Channel Mutation in Neonatal Human Epilepsy", C. Biervert et al. SCIENCE, vol. 279, Jan. 16, 1998 pp. 403–406.

"Moderate loss of function of cyclic–AMP–modulated KCNQ2/KCNQ3 K$^+$channels causes epilepsy", B. Schroeder et al., NATURE, vol. 396, Dec. 17, 1998 pp. 687–690.

* cited by examiner

*Primary Examiner*—Lorraine Spector
*Assistant Examiner*—Joseph F. Murphy
(74) *Attorney, Agent, or Firm*—Birch, Stewart, Kolasch & Birch, LLP

(57) ABSTRACT

This invention relates to novel potassium channels and genes encoding these channels. More specifically the invention provides isolated polynucleotides encoding the KCNQ4 potassium channel, cells transformed with these polynucleotides, transgenic animals comprising genetic mutations, and the use of the transformed cells and the transgenic animals for the in vitro and in vivo screening of drugs affecting KCNQ4 containing potassium channels.

24 Claims, 4 Drawing Sheets

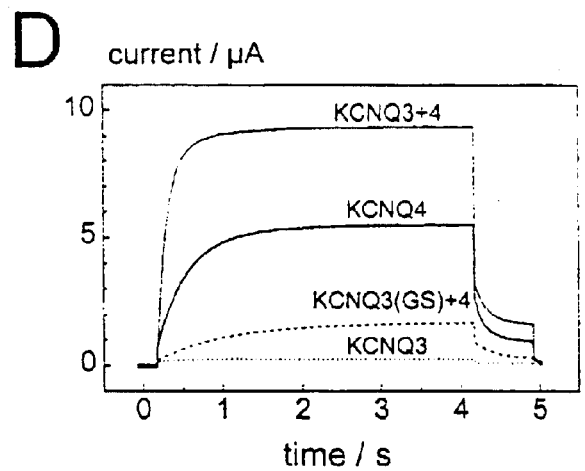
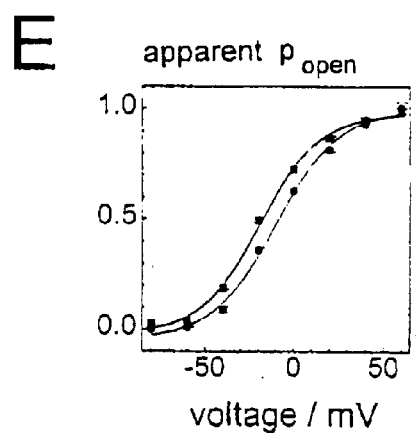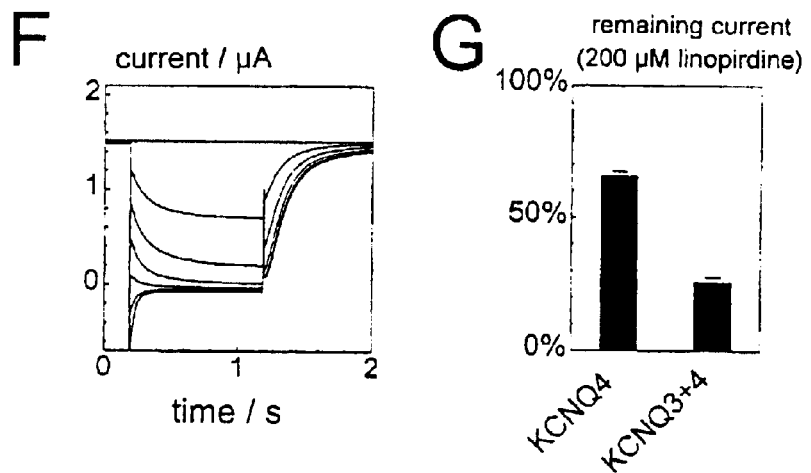
Fig. 2D-2G

SEQUENCE LISTING

<160> NUMBER OF SEQ ID NOS: 41

<210> SEQ ID NO 1
<211> LENGTH: 2335
<212> TYPE: DNA
<213> ORGANISM: Homo sapiens
<220> FEATURE:
<221> NAME/KEY: gene
<222> LOCATION: (1)..(2335)
<221> NAME/KEY: CDS
<222> LOCATION: (83)..(2170)

<400> SEQUENCE: 1

```
agccatgcgt ctctgagcgc cccgagcgcg ccccgcccc ggaccgtgcc cgggccccgg      60
cgcccccagc ccggcgccgc cc atg gcc gag gcc ccc ccg cgc cgc ctc ggc     112
                         Met Ala Glu Ala Pro Pro Arg Arg Leu Gly
                           1               5                  10 ctg ggt ccc ccg ccc ggg gac gcc ccc cgc gcg gag cta gtg gcg ctc      160
Leu Gly Pro Pro Pro Gly Asp Ala Pro Arg Ala Glu Leu Val Ala Leu
             15                  20                  25 acg gcc gtg cag agc gaa cag ggc gag gcg ggc ggg ggc tcc ccg         208
Thr Ala Val Gln Ser Glu Gln Gly Glu Ala Gly Gly Gly Ser Pro
         30                  35                  40
```

-continued

| | |
|---|---|
| cgc cgc ctc ggc ctc ctg ggc agc ccc ctg ccg ccg ggc gcg ccc ctc<br>Arg Arg Leu Gly Leu Leu Gly Ser Pro Leu Pro Pro Gly Ala Pro Leu<br>                45                          50                        55 | 256 |
| cct ggg ccg ggc tcc ggc tcg ggc tcc gcc tgc ggc cag cgc tcc tcg<br>Pro Gly Pro Gly Ser Gly Ser Gly Ser Ala Cys Gly Gln Arg Ser Ser<br>                60                          65                        70 | 304 |
| gcc gcg cac aag cgc tac cgc cgc ctg cag aac tgg gtc tac aac gtg<br>Ala Ala His Lys Arg Tyr Arg Arg Leu Gln Asn Trp Val Tyr Asn Val<br>75                          80                          85                        90 | 352 |
| ctg gag cgg ccc cgc ggc tgg gcc ttc gtc tac cac gtc ttc ata ttt<br>Leu Glu Arg Pro Arg Gly Trp Ala Phe Val Tyr His Val Phe Ile Phe<br>                95                        100                      105 | 400 |
| ttg ctg gtc ttc agc tgc ctg gtg ctg tct gtg ctg tcc act atc cag<br>Leu Leu Val Phe Ser Cys Leu Val Leu Ser Val Leu Ser Thr Ile Gln<br>                  110                        115                      120 | 448 |
| gag cac cag gaa ctt gcc aac gag tgt ctc ctc atc ttg gaa ttc gtg<br>Glu His Gln Glu Leu Ala Asn Glu Cys Leu Leu Ile Leu Glu Phe Val<br>                125                        130                      135 | 496 |
| atg atc gtg gtt ttc ggc ttg gag tac atc gtc cgg gtc tgg tcc gcc<br>Met Ile Val Val Phe Gly Leu Glu Tyr Ile Val Arg Val Trp Ser Ala<br>140                          145                        150 | 544 |
| gga tgc tgc tgc cgc tac cga gga tgg cag ggt cgc ttc cgc ttt gcc<br>Gly Cys Cys Cys Arg Tyr Arg Gly Trp Gln Gly Arg Phe Arg Phe Ala<br>155                          160                        165                      170 | 592 |
| aga aag ccc ttc tgt gtc atc gac ttc atc gtg ttc gtg gcc tcg gtg<br>Arg Lys Pro Phe Cys Val Ile Asp Phe Ile Val Phe Val Ala Ser Val<br>                  175                        180                      185 | 640 |
| gcc gtc atc gcc gcg ggt acc cag ggc aac atc ttc gcc acg tcc gcg<br>Ala Val Ile Ala Ala Gly Thr Gln Gly Asn Ile Phe Ala Thr Ser Ala<br>                  190                        195                      200 | 688 |
| ctg cgc agc atg cgc ttc ctg cag atc ctg cgc atg gtg cgc atg gac<br>Leu Arg Ser Met Arg Phe Leu Gln Ile Leu Arg Met Val Arg Met Asp<br>                  205                        210                      215 | 736 |
| cgc cgc ggc ggc acc tgg aag ctg ctg ggc tca gtg gtc tac gcg cat<br>Arg Arg Gly Gly Thr Trp Lys Leu Leu Gly Ser Val Val Tyr Ala His<br>220                          225                        230 | 784 |
| agc aag gag ctg atc acc gcc tgg tac atc ggg ttc ctg gtg ctc atc<br>Ser Lys Glu Leu Ile Thr Ala Trp Tyr Ile Gly Phe Leu Val Leu Ile<br>235                          240                        245                      250 | 832 |
| ttc gcc tcc ttc ctg gtc tac ctg gcc gag aag gac gcc aac tcc gac<br>Phe Ala Ser Phe Leu Val Tyr Leu Ala Glu Lys Asp Ala Asn Ser Asp<br>                  255                        260                      265 | 880 |
| ttc tcc tcc tac gcc gac tcg ctc tgg tgg ggg acg att aca ttg aca<br>Phe Ser Ser Tyr Ala Asp Ser Leu Trp Trp Gly Thr Ile Thr Leu Thr<br>                  270                        275                      280 | 928 |
| acc atc ggc tat ggt gac aag aca ccg cac aca tgg ctg ggc agg gtc<br>Thr Ile Gly Tyr Gly Asp Lys Thr Pro His Thr Trp Leu Gly Arg Val<br>                  285                        290                      295 | 976 |
| ctg gct gct ggc ttc gcc tta ctg ggc atc tct ttc ttt gcc ctg cct<br>Leu Ala Ala Gly Phe Ala Leu Leu Gly Ile Ser Phe Phe Ala Leu Pro<br>300                          305                        310 | 1024 |
| gcc ggc atc cta ggc tcc ggc ttt gcc ctg aag gtc cag gag cag cac<br>Ala Gly Ile Leu Gly Ser Gly Phe Ala Leu Lys Val Gln Glu Gln His<br>315                          320                        325                      330 | 1072 |
| cgg cag aag cac ttc gag aag cgg agg atg ccg gca gcc aac ctc atc<br>Arg Gln Lys His Phe Glu Lys Arg Arg Met Pro Ala Ala Asn Leu Ile<br>                  335                        340                      345 | 1120 |

-continued

| | |
|---|---|
| cag gct gcc tgg cgc ctg tac tcc acc gat atg agc cgg gcc tac ctg<br>Gln Ala Ala Trp Arg Leu Tyr Ser Thr Asp Met Ser Arg Ala Tyr Leu<br>350 355 360 | 1168 |
| aca gcc acc tgg tac tac tat gac agt atc ctc cca tcc ttc aga gag<br>Thr Ala Thr Trp Tyr Tyr Tyr Asp Ser Ile Leu Pro Ser Phe Arg Glu<br>365 370 375 | 1216 |
| ctg gcc ctc ttg ttt gag cac gtg caa cgg gcc cgc aat ggg ggc cta<br>Leu Ala Leu Leu Phe Glu His Val Gln Arg Ala Arg Asn Gly Gly Leu<br>380 385 390 | 1264 |
| cgg ccc ctg gag gtg cgg cgg gcg ccg gta ccc gac gga gca ccc tcc<br>Arg Pro Leu Glu Val Arg Arg Ala Pro Val Pro Asp Gly Ala Pro Ser<br>395 400 405 410 | 1312 |
| cgt tac ccg ccc gtt gcc acc tgc cac cgg ccg ggc agc acc tcc ttc<br>Arg Tyr Pro Pro Val Ala Thr Cys His Arg Pro Gly Ser Thr Ser Phe<br>415 420 425 | 1360 |
| tgc cct ggg gaa agc agc cgg atg ggc atc aaa gac cgc atc cgc atg<br>Cys Pro Gly Glu Ser Ser Arg Met Gly Ile Lys Asp Arg Ile Arg Met<br>430 435 440 | 1408 |
| ggc agc tcc cag cgg cgg acg ggt cct tcc aag cag cag ctg gca cct<br>Gly Ser Ser Gln Arg Arg Thr Gly Pro Ser Lys Gln Gln Leu Ala Pro<br>445 450 455 | 1456 |
| cca aca atg ccc acc tcc cca agc agc gag cag gtg ggt gag gcc acc<br>Pro Thr Met Pro Thr Ser Pro Ser Ser Glu Gln Val Gly Glu Ala Thr<br>460 465 470 | 1504 |
| agc ccc acc aag gtg caa aag agc tgg agc ttc aat gac cgc acc cgc<br>Ser Pro Thr Lys Val Gln Lys Ser Trp Ser Phe Asn Asp Arg Thr Arg<br>475 480 485 490 | 1552 |
| ttc cgg gca tct ctg aga ctc aaa ccc cgc acc tct gct gag gat gcc<br>Phe Arg Ala Ser Leu Arg Leu Lys Pro Arg Thr Ser Ala Glu Asp Ala<br>495 500 505 | 1600 |
| ccc tca gag gaa gta gca gag gag aag agc tac cag tgt gag ctc acg<br>Pro Ser Glu Glu Val Ala Glu Glu Lys Ser Tyr Gln Cys Glu Leu Thr<br>510 515 520 | 1648 |
| gtg gac gac atc atg cct gct gtg aag aca gtc atc cgc tcc atc agg<br>Val Asp Asp Ile Met Pro Ala Val Lys Thr Val Ile Arg Ser Ile Arg<br>525 530 535 | 1696 |
| att ctc aag ttc ctg gtg gcc aaa agg aaa ttc aag gag aca ctg cga<br>Ile Leu Lys Phe Leu Val Ala Lys Arg Lys Phe Lys Glu Thr Leu Arg<br>540 545 550 | 1744 |
| ccg tac gac gtg aag gac gtc att gag cag tac tca gca ggc cac ctg<br>Pro Tyr Asp Val Lys Asp Val Ile Glu Gln Tyr Ser Ala Gly His Leu<br>555 560 565 570 | 1792 |
| gac atg ctg ggc cgg atc aag agc ctg caa act cgg gtg gac caa att<br>Asp Met Leu Gly Arg Ile Lys Ser Leu Gln Thr Arg Val Asp Gln Ile<br>575 580 585 | 1840 |
| gtg ggt cgg ggg ccc ggg gac agg aag gcc cgg gag aag ggc gac aag<br>Val Gly Arg Gly Pro Gly Asp Arg Lys Ala Arg Glu Lys Gly Asp Lys<br>590 595 600 | 1888 |
| ggg ccc tcc gac gcg gag gtg gtg gat gaa atc agc atg atg gga cgc<br>Gly Pro Ser Asp Ala Glu Val Val Asp Glu Ile Ser Met Met Gly Arg<br>605 610 615 | 1936 |
| gtg gtc aag gtg gag aag cag gtg cag tcc atc gag cac aag ctg gac<br>Val Val Lys Val Glu Lys Gln Val Gln Ser Ile Glu His Lys Leu Asp<br>620 625 630 | 1984 |
| ctg ctg ttg ggc ttc tat tcg cgc tgc ctg cgc tct ggc acc tcg gcc<br>Leu Leu Leu Gly Phe Tyr Ser Arg Cys Leu Arg Ser Gly Thr Ser Ala<br>635 640 645 650 | 2032 |
| agc ctg ggc gcc gtg caa gtg ccg ctg ttc gac ccc gac atc acc tcc<br>Ser Leu Gly Ala Val Gln Val Pro Leu Phe Asp Pro Asp Ile Thr Ser<br>655 660 665 | 2080 |

-continued

```
gac tac cac agc cct gtg gac cac gag gac atc tcc gtc tcc gca cag    2128
Asp Tyr His Ser Pro Val Asp His Glu Asp Ile Ser Val Ser Ala Gln
            670                 675                 680 acg ctc agc atc tcc cgc tcg gtc agc acc aac atg gac tga            2170
Thr Leu Ser Ile Ser Arg Ser Val Ser Thr Asn Met Asp
        685                 690                 695 gggacttctc agaggcaggg cagcacacgg ccagccccgc ggcctggcgc tccgactgcc   2230
ctctgaggcc tccggactcc tctcgtactt gaactcactc cctcacgggg agagagacca   2290
cacgcagtat tgagctgcct gagtgggcgt ggtacctgct gtggg                  2335
```

<210> SEQ ID NO 2
<211> LENGTH: 695
<212> TYPE: PRT
<213> ORGANISM: Homo sapiens

<400> SEQUENCE: 2

```
Met Ala Glu Ala Pro Pro Arg Arg Leu Gly Leu Gly Pro Pro Pro Gly
  1               5                  10                  15

Asp Ala Pro Arg Ala Glu Leu Val Ala Leu Thr Ala Val Gln Ser Glu
             20                  25                  30

Gln Gly Glu Ala Gly Gly Gly Ser Pro Arg Arg Leu Gly Leu Leu
         35                  40                  45

Gly Ser Pro Leu Pro Pro Gly Ala Pro Leu Pro Gly Pro Gly Ser Gly
     50                  55                  60

Ser Gly Ser Ala Cys Gly Gln Arg Ser Ser Ala Ala His Lys Arg Tyr
 65                  70                  75                  80

Arg Arg Leu Gln Asn Trp Val Tyr Asn Val Leu Glu Arg Pro Arg Gly
                 85                  90                  95

Trp Ala Phe Val Tyr His Val Phe Ile Phe Leu Leu Val Phe Ser Cys
            100                 105                 110

Leu Val Leu Ser Val Leu Ser Thr Ile Gln Glu His Gln Glu Leu Ala
        115                 120                 125

Asn Glu Cys Leu Leu Ile Leu Glu Phe Val Met Ile Val Val Phe Gly
    130                 135                 140

Leu Glu Tyr Ile Val Arg Val Trp Ser Ala Gly Cys Cys Cys Arg Tyr
145                 150                 155                 160

Arg Gly Trp Gln Gly Arg Phe Arg Phe Ala Arg Lys Pro Phe Cys Val
                165                 170                 175

Ile Asp Phe Ile Val Phe Val Ala Ser Val Ala Val Ile Ala Ala Gly
            180                 185                 190

Thr Gln Gly Asn Ile Phe Ala Thr Ser Ala Leu Arg Ser Met Arg Phe
        195                 200                 205

Leu Gln Ile Leu Arg Met Val Arg Met Asp Arg Arg Gly Gly Thr Trp
    210                 215                 220

Lys Leu Leu Gly Ser Val Val Tyr Ala His Ser Lys Glu Leu Ile Thr
225                 230                 235                 240

Ala Trp Tyr Ile Gly Phe Leu Val Leu Ile Phe Ala Ser Phe Leu Val
                245                 250                 255

Tyr Leu Ala Glu Lys Asp Ala Asn Ser Asp Phe Ser Ser Tyr Ala Asp
            260                 265                 270

Ser Leu Trp Trp Gly Thr Ile Thr Leu Thr Thr Ile Gly Tyr Gly Asp
        275                 280                 285

Lys Thr Pro His Thr Trp Leu Gly Arg Val Leu Ala Ala Gly Phe Ala
    290                 295                 300
```

-continued

```
Leu Leu Gly Ile Ser Phe Phe Ala Leu Pro Ala Gly Ile Leu Gly Ser
305                 310                 315                 320

Gly Phe Ala Leu Lys Val Gln Glu Gln His Arg Gln Lys His Phe Glu
                325                 330                 335

Lys Arg Arg Met Pro Ala Ala Asn Leu Ile Gln Ala Ala Trp Arg Leu
            340                 345                 350

Tyr Ser Thr Asp Met Ser Arg Ala Tyr Leu Thr Ala Thr Trp Tyr Tyr
        355                 360                 365

Tyr Asp Ser Ile Leu Pro Ser Phe Arg Glu Leu Ala Leu Leu Phe Glu
    370                 375                 380

His Val Gln Arg Ala Arg Asn Gly Gly Leu Arg Pro Leu Glu Val Arg
385                 390                 395                 400

Arg Ala Pro Val Pro Asp Gly Ala Pro Ser Arg Tyr Pro Pro Val Ala
                405                 410                 415

Thr Cys His Arg Pro Gly Ser Thr Ser Phe Cys Pro Gly Glu Ser Ser
            420                 425                 430

Arg Met Gly Ile Lys Asp Arg Ile Arg Met Gly Ser Ser Gln Arg Arg
        435                 440                 445

Thr Gly Pro Ser Lys Gln Gln Leu Ala Pro Pro Thr Met Pro Thr Ser
    450                 455                 460

Pro Ser Ser Glu Gln Val Gly Glu Ala Thr Ser Pro Thr Lys Val Gln
465                 470                 475                 480

Lys Ser Trp Ser Phe Asn Asp Arg Thr Arg Phe Arg Ala Ser Leu Arg
                485                 490                 495

Leu Lys Pro Arg Thr Ser Ala Glu Asp Ala Pro Ser Glu Glu Val Ala
            500                 505                 510

Glu Glu Lys Ser Tyr Gln Cys Glu Leu Thr Val Asp Asp Ile Met Pro
        515                 520                 525

Ala Val Lys Thr Val Ile Arg Ser Ile Arg Ile Leu Lys Phe Leu Val
    530                 535                 540

Ala Lys Arg Lys Phe Lys Glu Thr Leu Arg Pro Tyr Asp Val Lys Asp
545                 550                 555                 560

Val Ile Glu Gln Tyr Ser Ala Gly His Leu Asp Met Leu Gly Arg Ile
                565                 570                 575

Lys Ser Leu Gln Thr Arg Val Asp Gln Ile Val Gly Arg Gly Pro Gly
            580                 585                 590

Asp Arg Lys Ala Arg Glu Lys Gly Asp Lys Gly Pro Ser Asp Ala Glu
        595                 600                 605

Val Val Asp Glu Ile Ser Met Met Gly Arg Val Val Lys Val Glu Lys
    610                 615                 620

Gln Val Gln Ser Ile Glu His Lys Leu Asp Leu Leu Leu Gly Phe Tyr
625                 630                 635                 640

Ser Arg Cys Leu Arg Ser Gly Thr Ser Ala Ser Leu Gly Ala Val Gln
                645                 650                 655

Val Pro Leu Phe Asp Pro Asp Ile Thr Ser Asp Tyr His Ser Pro Val
            660                 665                 670

Asp His Glu Asp Ile Ser Val Ser Ala Gln Thr Leu Ser Ile Ser Arg
        675                 680                 685

Ser Val Ser Thr Asn Met Asp
690                 695
```

```
<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 3
catgcgtctc tgagcgcccc gagc                                          24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 4
aggccaggct tgcgcgggga aacg                                          24

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: PCR Primer

<400> SEQUENCE: 5
cagcacagag ctgtaactcc agg                                           23

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: PCR Primer

<400> SEQUENCE: 6
aagctgctct ctgagccatg g                                             21

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 7
gctgggtccg cgctgtgacc                                               20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 8
ggtctccagg gtcagagtcg                                               20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: PCR Primer
```

```
<400> SEQUENCE: 9
tccgggtccg tgcgcggggt a                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: PCR Primer

<400> SEQUENCE: 10
gagacagccc ctctgacctc g                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: PCR Primer

<400> SEQUENCE: 11
atccctttcc cgtgtggaag c                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: PCR Primer

<400> SEQUENCE: 12
agtcacgatg ggcagacctc g                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: PCR Primer

<400> SEQUENCE: 13
cctcatgatc aggctcctac c                                              21

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: PCR Primer

<400> SEQUENCE: 14
atgtgtgaca ggggtgagc                                                 19

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 15
aaggatgggg acacccttgc                                                20
```

```
<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: PCR Primer

<400> SEQUENCE: 16
acacagggtt gacacacc                                                       18

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: PCR Primer

<400> SEQUENCE: 17
gctctgggta acccacaact g                                                   21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: PCR Primer

<400> SEQUENCE: 18
gctcccctgg gagccatcac c                                                   21

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 19
tgagctcagg agctctgtgc                                                     20

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: PCR Primer

<400> SEQUENCE: 20
acccacgaag tggctgaagg c                                                   21

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 21
gtcctaagtc agctttgtcc                                                     20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: PCR Primer
```

<400> SEQUENCE: 22
cctcagccgg ccctcgatcg                      20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 23
cactctactg gtggtttggc                      20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 24
ctcctgacct caagtgatcc                      20

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: PCR Primer

<400> SEQUENCE: 25
gatagcaaag agatggagag g                    21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: PCR Primer

<400> SEQUENCE: 26
aactcagctg cagcagtgag c                    21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: PCR Primer

<400> SEQUENCE: 27
gtgccttctc cttcatcagg c                    21

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 28
aacgcatcct ccccatgtca                      20

-continued

```
<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 29
tttgtgcttc ccagataagc                                                    20

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 30
cgtgagggag tgagttcaag tacg                                               24

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 31
agtacctgat ggagcgccct ctcg                                               24

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 32
tcatccaccg taagctcaca ctgg                                               24

<210> SEQ ID NO 33
<211> LENGTH: 676
<212> TYPE: PRT
<213> ORGANISM: Homo sapiens

<400> SEQUENCE: 33

Met Ala Ala Ser Ser Pro Pro Arg Ala Glu Arg Lys Arg Trp Gly
 1               5                  10                  15

Trp Gly Arg Leu Pro Gly Ala Arg Arg Gly Ser Ala Gly Leu Ala Lys
            20                  25                  30

Lys Cys Pro Phe Ser Leu Glu Leu Ala Glu Gly Gly Pro Ala Gly Gly
        35                  40                  45

Ala Leu Tyr Ala Pro Ile Ala Pro Gly Ala Pro Gly Pro Ala Pro Pro
    50                  55                  60

Ala Ser Pro Ala Ala Pro Ala Ala Pro Pro Val Ala Ser Asp Leu Gly
65                  70                  75                  80

Pro Arg Pro Pro Val Ser Leu Asp Pro Arg Val Ser Ile Tyr Ser Thr
                85                  90                  95

Arg Arg Pro Val Leu Ala Arg Thr His Val Gln Gly Arg Val Tyr Asn
            100                 105                 110

Phe Leu Glu Arg Pro Thr Gly Trp Lys Cys Phe Val Tyr His Phe Ala
        115                 120                 125
```

-continued

```
Val Phe Leu Ile Val Leu Val Cys Leu Ile Phe Ser Val Leu Ser Thr
    130                 135                 140

Ile Glu Gln Tyr Ala Ala Leu Ala Thr Gly Thr Leu Phe Trp Met Glu
145                 150                 155                 160

Ile Val Leu Val Val Phe Phe Gly Thr Glu Tyr Val Val Arg Leu Trp
                    165                 170                 175

Ser Ala Gly Cys Arg Ser Lys Tyr Val Gly Leu Trp Gly Arg Leu Arg
                180                 185                 190

Phe Ala Arg Lys Pro Ile Ser Ile Asp Leu Ile Val Val Ala
            195                 200                 205

Ser Met Val Val Leu Cys Val Gly Ser Lys Gly Gln Val Phe Ala Thr
    210                 215                 220

Ser Ala Ile Arg Gly Ile Arg Phe Leu Gln Ile Leu Arg Met Leu His
225                 230                 235                 240

Val Asp Arg Gln Gly Gly Thr Trp Arg Leu Leu Gly Ser Val Val Phe
                245                 250                 255

Ile His Arg Gln Glu Leu Ile Thr Thr Leu Tyr Ile Gly Phe Leu Gly
                260                 265                 270

Leu Ile Phe Ser Ser Tyr Phe Val Tyr Leu Ala Glu Lys Asp Ala Val
            275                 280                 285

Asn Glu Ser Gly Arg Val Glu Phe Gly Ser Tyr Ala Asp Ala Leu Trp
290                 295                 300

Trp Gly Val Val Thr Val Thr Thr Ile Gly Tyr Gly Asp Lys Val Pro
305                 310                 315                 320

Gln Thr Trp Val Gly Lys Thr Ile Ala Ser Cys Phe Ser Val Phe Ala
                325                 330                 335

Ile Ser Phe Phe Ala Leu Pro Ala Gly Ile Leu Gly Ser Gly Phe Ala
            340                 345                 350

Leu Lys Val Gln Gln Lys Gln Arg Gln Lys His Phe Asn Arg Gln Ile
            355                 360                 365

Pro Ala Ala Ala Ser Leu Ile Gln Thr Ala Trp Arg Cys Tyr Ala Ala
370                 375                 380

Glu Asn Pro Asp Ser Ser Thr Trp Lys Ile Tyr Ile Arg Lys Ala Pro
385                 390                 395                 400

Arg Ser His Thr Leu Leu Ser Pro Ser Pro Lys Pro Lys Lys Ser Val
                405                 410                 415

Val Val Lys Lys Lys Lys Phe Lys Leu Asp Lys Asp Asn Gly Val Thr
            420                 425                 430

Pro Gly Glu Lys Met Leu Thr Val Pro His Ile Thr Cys Asp Pro Pro
            435                 440                 445

Glu Glu Arg Arg Leu Asp His Phe Ser Val Asp Gly Tyr Asp Ser Ser
450                 455                 460

Val Arg Lys Ser Pro Thr Leu Leu Glu Val Ser Met Pro His Phe Met
465                 470                 475                 480

Arg Thr Asn Ser Phe Ala Glu Asp Leu Asp Leu Glu Gly Glu Thr Leu
                485                 490                 495

Leu Thr Pro Ile Thr His Ile Ser Gln Leu Arg Glu His His Arg Ala
            500                 505                 510

Thr Ile Lys Val Ile Arg Arg Met Gln Tyr Phe Val Ala Lys Lys Lys
            515                 520                 525

Phe Gln Gln Ala Arg Lys Pro Tyr Asp Val Arg Asp Val Ile Glu Gln
530                 535                 540
```

-continued

Tyr Ser Gln Gly His Leu Asn Leu Met Val Arg Ile Lys Glu Leu Gln
545                 550                 555                 560

Arg Arg Leu Asp Gln Ser Ile Gly Lys Pro Ser Leu Phe Ile Ser Val
                565                 570                 575

Ser Glu Lys Ser Lys Asp Arg Gly Ser Asn Thr Ile Gly Ala Arg Leu
                580                 585                 590

Asn Arg Val Glu Asp Lys Val Thr Gln Leu Asp Gln Arg Leu Ala Leu
                595                 600                 605

Ile Thr Asp Met Leu His Gln Leu Leu Ser Leu His Gly Gly Ser Thr
                610                 615                 620

Pro Gly Ser Gly Gly Pro Arg Glu Gly Gly Ala His Ile Thr Gln
625                 630                 635                 640

Pro Cys Gly Ser Gly Gly Ser Val Asp Pro Glu Leu Phe Leu Pro Ser
                645                 650                 655

Asn Thr Leu Pro Thr Tyr Glu Gln Leu Thr Val Pro Arg Arg Gly Pro
                660                 665                 670

Asp Glu Gly Ser
        675

<210> SEQ ID NO 34
<211> LENGTH: 844
<212> TYPE: PRT
<213> ORGANISM: Homo sapiens

<400> SEQUENCE: 34

Met Val Gln Lys Ser Arg Asn Gly Gly Val Tyr Pro Gly Pro Ser Gly
1               5                   10                  15

Glu Lys Lys Leu Lys Val Gly Phe Val Gly Leu Asp Pro Gly Ala Pro
                20                  25                  30

Asp Ser Thr Arg Asp Gly Ala Leu Leu Ile Ala Gly Ser Glu Ala Pro
                35                  40                  45

Lys Arg Gly Ser Ile Leu Ser Lys Pro Arg Ala Gly Ala Gly Ala
            50                  55                  60

Gly Lys Pro Pro Lys Arg Asn Ala Phe Tyr Arg Lys Leu Gln Asn Phe
65                  70                  75                  80

Leu Tyr Asn Val Leu Glu Arg Pro Arg Gly Trp Ala Phe Ile Tyr His
                85                  90                  95

Ala Tyr Val Phe Leu Leu Val Phe Ser Cys Leu Val Leu Ser Val Phe
                100                 105                 110

Ser Thr Ile Lys Glu Tyr Glu Lys Ser Ser Glu Gly Ala Leu Tyr Ile
                115                 120                 125

Leu Glu Ile Val Thr Ile Val Val Phe Gly Val Glu Tyr Phe Val Arg
                130                 135                 140

Ile Trp Ala Ala Gly Cys Cys Cys Arg Tyr Arg Gly Trp Arg Gly Arg
145                 150                 155                 160

Leu Lys Phe Ala Arg Lys Pro Phe Cys Val Ile Asp Ile Met Val Leu
                165                 170                 175

Ile Ala Ser Ile Ala Val Leu Ala Ala Gly Ser Gln Gly Asn Val Phe
                180                 185                 190

Ala Thr Ser Ala Leu Arg Ser Leu Arg Phe Leu Gln Ile Leu Arg Met
                195                 200                 205

Ile Arg Met Asp Arg Arg Gly Gly Thr Trp Lys Leu Leu Gly Ser Val
                210                 215                 220

Val Tyr Ala His Ser Lys Glu Leu Val Thr Ala Trp Tyr Ile Gly Phe
225                 230                 235                 240

-continued

```
Leu Cys Leu Ile Leu Ala Ser Phe Leu Val Tyr Leu Ala Glu Lys Gly
            245                 250                 255

Glu Asn Asp His Phe Asp Thr Tyr Ala Asp Ala Leu Trp Trp Gly Leu
            260                 265                 270

Ile Thr Leu Thr Thr Ile Gly Tyr Gly Asp Lys Tyr Pro Gln Thr Trp
            275                 280                 285

Asn Gly Arg Leu Leu Ala Ala Thr Phe Thr Leu Ile Gly Val Ser Phe
290                 295                 300

Phe Ala Leu Pro Ala Gly Ile Leu Gly Ser Gly Phe Ala Leu Lys Val
305                 310                 315                 320

Gln Glu Gln His Arg Gln Lys His Phe Glu Lys Arg Arg Asn Pro Ala
                325                 330                 335

Ala Gly Leu Ile Gln Ser Ala Trp Arg Phe Tyr Ala Thr Asn Leu Ser
                340                 345                 350

Arg Thr Asp Leu His Ser Thr Trp Gln Tyr Tyr Glu Arg Thr Val Thr
            355                 360                 365

Val Pro Met Tyr Arg Leu Ile Pro Pro Leu Asn Gln Leu Glu Leu Leu
        370                 375                 380

Arg Asn Leu Lys Ser Lys Ser Gly Leu Ala Phe Arg Lys Asp Pro Pro
385                 390                 395                 400

Pro Glu Pro Ser Pro Ser Gln Lys Val Ser Leu Lys Asp Arg Val Phe
                405                 410                 415

Ser Ser Pro Arg Gly Val Ala Ala Lys Gly Lys Gly Ser Pro Gln Ala
                420                 425                 430

Gln Thr Val Arg Arg Ser Pro Ser Ala Asp Gln Ser Leu Glu Asp Ser
            435                 440                 445

Pro Ser Lys Val Pro Lys Ser Trp Ser Phe Gly Asp Arg Ser Arg Ala
        450                 455                 460

Arg Gln Ala Phe Arg Ile Lys Gly Ala Ala Ser Arg Gln Asn Ser Glu
465                 470                 475                 480

Glu Ala Ser Leu Pro Gly Glu Asp Ile Val Asp Lys Ser Cys Pro
                485                 490                 495

Cys Glu Phe Val Thr Glu Asp Leu Thr Pro Gly Leu Lys Val Ser Ile
                500                 505                 510

Arg Ala Val Cys Val Met Arg Phe Leu Val Ser Lys Arg Lys Phe Lys
            515                 520                 525

Glu Ser Leu Arg Pro Tyr Asp Val Met Asp Val Ile Glu Gln Tyr Ser
        530                 535                 540

Ala Gly His Leu Asp Met Leu Ser Arg Ile Lys Ser Leu Gln Ser Arg
545                 550                 555                 560

Val Asp Gln Ile Val Gly Arg Gly Pro Ala Ile Thr Asp Lys Asp Arg
                565                 570                 575

Thr Lys Gly Pro Ala Glu Ala Glu Leu Pro Glu Asp Pro Ser Met Met
            580                 585                 590

Gly Arg Leu Gly Lys Val Glu Lys Gln Val Leu Ser Met Glu Lys Lys
        595                 600                 605

Leu Asp Phe Leu Val Asn Ile Tyr Met Gln Arg Met Gly Ile Pro Pro
        610                 615                 620

Thr Glu Thr Glu Ala Tyr Phe Gly Ala Lys Glu Pro Glu Pro Ala Pro
625                 630                 635                 640

Pro Tyr His Ser Pro Glu Asp Ser Arg Glu His Val Asp Arg His Gly
                645                 650                 655
```

-continued

```
Cys Ile Val Lys Ile Val Arg Ser Ser Ser Thr Gly Gln Lys Asn
            660                 665                 670

Phe Ser Ala Pro Pro Ala Ala Pro Val Gln Cys Pro Pro Ser Thr
        675                 680                 685

Ser Trp Gln Pro Gln Ser His Pro Arg Gln Gly His Gly Thr Ser Pro
    690                 695                 700

Val Gly Asp His Gly Ser Leu Val Arg Ile Pro Pro Pro Ala His
705                 710                 715                 720

Glu Arg Ser Leu Ser Ala Tyr Gly Gly Asn Arg Ala Ser Met Glu
                725                 730                 735

Phe Leu Arg Gln Glu Asp Thr Pro Gly Cys Arg Pro Pro Glu Gly Thr
            740                 745                 750

Leu Arg Asp Ser Asp Thr Ser Ile Ser Ile Pro Ser Val Asp His Glu
            755                 760                 765

Glu Leu Glu Arg Ser Phe Ser Gly Phe Ser Ile Ser Gln Ser Lys Glu
        770                 775                 780

Asn Leu Asp Ala Leu Asn Ser Cys Tyr Ala Ala Val Ala Pro Cys Ala
785                 790                 795                 800

Lys Val Arg Pro Tyr Ile Ala Glu Gly Glu Ser Asp Thr Asp Ser Asp
                805                 810                 815

Leu Cys Thr Pro Cys Gly Pro Pro Arg Ser Ala Thr Gly Glu Gly
            820                 825                 830

Pro Phe Gly Asp Val Gly Trp Ala Gly Pro Arg Lys
        835                 840

<210> SEQ ID NO 35
<211> LENGTH: 872
<212> TYPE: PRT
<213> ORGANISM: Homo sapiens

<400> SEQUENCE: 35

Met Gly Leu Lys Ala Arg Arg Ala Ala Gly Ala Gly Gly Gly Gly
  1               5                  10                  15

Asp Gly Gly Gly Gly Gly Gly Ala Ala Asn Pro Ala Gly Gly Asp
                20                  25                  30

Ala Ala Ala Ala Gly Asp Glu Glu Arg Lys Val Gly Leu Ala Pro Gly
            35                  40                  45

Asp Val Glu Gln Val Thr Leu Ala Leu Gly Gly Ala Asp Lys Asp
     50                  55                  60

Gly Thr Leu Leu Leu Glu Gly Gly Arg Asp Glu Gly Gln Arg Arg
 65                  70                  75                  80

Thr Pro Gln Gly Ile Gly Leu Leu Ala Lys Thr Pro Leu Ser Arg Pro
                85                  90                  95

Val Lys Arg Asn Asn Ala Lys Tyr Arg Arg Ile Gln Thr Leu Ile Tyr
            100                 105                 110

Asp Ala Leu Glu Arg Pro Arg Gly Trp Ala Leu Leu Tyr His Ala Leu
        115                 120                 125

Val Phe Leu Ile Val Leu Gly Cys Leu Ile Leu Ala Val Leu Thr Thr
Phe Lys Glu Tyr Glu Thr Val Ser Gly Asp Trp Leu Leu Leu Glu
145                 150                 155                 160

Thr Phe Ala Ile Phe Ile Phe Gly Ala Glu Phe Ala Leu Arg Ile Trp
                165                 170                 175

Ala Ala Gly Cys Cys Cys Arg Tyr Lys Gly Trp Arg Gly Arg Leu Lys
            180                 185                 190
```

```
Phe Ala Arg Lys Pro Leu Cys Met Leu Asp Ile Phe Val Leu Ile Ala
            195                 200                 205

Ser Val Pro Val Ala Val Gly Asn Gln Gly Asn Val Leu Ala Thr
        210                 215                 220

Ser Leu Arg Ser Leu Arg Phe Leu Gln Ile Leu Arg Met Leu Arg Met
225                 230                 235                 240

Asp Arg Arg Gly Gly Thr Trp Lys Leu Leu Gly Ser Ala Ile Cys Ala
                245                 250                 255

His Ser Lys Glu Leu Ile Thr Ala Trp Tyr Ile Gly Phe Leu Thr Leu
            260                 265                 270

Ile Leu Ser Ser Phe Leu Val Tyr Leu Val Glu Lys Asp Val Pro Glu
            275                 280                 285

Val Asp Ala Gln Gly Glu Glu Met Lys Glu Glu Phe Glu Thr Tyr Ala
        290                 295                 300

Asp Ala Leu Trp Trp Gly Leu Ile Thr Leu Ala Thr Ile Gly Tyr Gly
305                 310                 315                 320

Asp Lys Thr Pro Lys Thr Trp Glu Gly Arg Leu Ile Ala Ala Thr Phe
                325                 330                 335

Ser Leu Ile Gly Val Ser Phe Phe Ala Leu Pro Ala Gly Ile Leu Gly
            340                 345                 350

Ser Gly Leu Ala Leu Lys Val Gln Glu Gln His Arg Gln Lys His Phe
        355                 360                 365

Glu Lys Arg Arg Lys Pro Ala Ala Glu Leu Ile Gln Ala Ala Trp Arg
        370                 375                 380

Tyr Tyr Ala Thr Asn Pro Asn Arg Ile Asp Leu Val Ala Thr Trp Arg
385                 390                 395                 400

Phe Tyr Glu Ser Val Val Ser Phe Pro Phe Phe Arg Lys Glu Gln Leu
                405                 410                 415

Glu Ala Ala Ser Ser Gln Lys Leu Gly Leu Leu Asp Arg Val Arg Leu
            420                 425                 430

Ser Asn Pro Arg Gly Ser Asn Thr Lys Gly Lys Leu Phe Thr Pro Leu
            435                 440                 445

Asn Val Asp Ala Ile Glu Glu Ser Pro Ser Lys Glu Pro Lys Pro Val
        450                 455                 460

Gly Leu Asn Asn Lys Glu Arg Phe Arg Thr Ala Phe Arg Met Lys Ala
465                 470                 475                 480

Tyr Ala Phe Trp Gln Ser Ser Glu Asp Ala Gly Thr Gly Asp Pro Met
                485                 490                 495

Ala Glu Asp Arg Gly Tyr Gly Asn Asp Phe Pro Ile Glu Asp Met Ile
            500                 505                 510

Pro Thr Leu Lys Ala Ala Ile Arg Ala Val Arg Ile Leu Gln Phe Arg
        515                 520                 525

Leu Tyr Lys Lys Lys Phe Lys Glu Thr Leu Arg Pro Tyr Asp Val Lys
        530                 535                 540

Asp Val Ile Glu Gln Tyr Ser Ala Gly His Leu Asp Met Leu Ser Arg
545                 550                 555                 560

Ile Lys Tyr Leu Gln Thr Arg Ile Asp Met Ile Phe Thr Pro Gly Pro
                565                 570                 575

Pro Ser Thr Pro Lys His Lys Lys Ser Gln Lys Gly Ser Ala Phe Thr
            580                 585                 590

Phe Pro Ser Gln Gln Ser Pro Arg Asn Glu Pro Tyr Val Ala Arg Pro
            595                 600                 605
```

-continued

```
Ser Thr Ser Glu Ile Glu Asp Gln Ser Met Met Gly Lys Phe Val Lys
    610                 615                 620

Val Glu Arg Gln Val Gln Asp Met Gly Lys Lys Leu Asp Phe Leu Val
625                 630                 635                 640

Asp Met His Met Gln His Met Glu Arg Leu Gln Val Gln Val Thr Glu
                645                 650                 655

Tyr Tyr Pro Thr Lys Gly Thr Ser Pro Ala Glu Ala Glu Lys Lys
            660                 665                 670

Glu Asp Asn Arg Tyr Ser Asp Leu Lys Thr Ile Ile Cys Asn Tyr Ser
                675                 680                 685

Glu Thr Gly Pro Pro Glu Pro Pro Tyr Ser Phe His Gln Val Thr Ile
    690                 695                 700

Asp Lys Val Ser Pro Tyr Gly Phe Phe Ala His Asp Pro Val Asn Leu
705                 710                 715                 720

Pro Arg Gly Gly Pro Ser Ser Gly Lys Val Gln Ala Thr Pro Pro Ser
                725                 730                 735

Ser Ala Thr Thr Tyr Val Glu Arg Pro Thr Val Leu Pro Ile Leu Thr
                740                 745                 750

Leu Leu Asp Ser Arg Val Ser Cys His Ser Gln Ala Asp Leu Gln Gly
    755                 760                 765

Pro Tyr Ser Asp Arg Ile Ser Pro Arg Gln Arg Ser Ile Thr Arg
    770                 775                 780

Asp Ser Asp Thr Pro Leu Ser Leu Met Ser Val Asn His Glu Glu Leu
785                 790                 795                 800

Glu Arg Ser Pro Ser Gly Phe Ser Ile Ser Gln Asp Arg Asp Asp Tyr
                805                 810                 815

Val Phe Gly Pro Asn Gly Gly Ser Ser Trp Met Arg Glu Lys Arg Tyr
                820                 825                 830

Leu Ala Glu Gly Glu Thr Asp Thr Asp Thr Asp Pro Phe Thr Pro Ser
    835                 840                 845

Gly Ser Met Pro Leu Ser Ser Thr Gly Asp Gly Ile Ser Asp Ser Val
    850                 855                 860

Trp Thr Pro Ser Asn Lys Pro Ile
865                 870
```

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: PCR Primer

<400> SEQUENCE: 36
aaggctggat cagtccattg g                                           21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: PCR Primer

<400> SEQUENCE: 37
aggtgggcag gctgttgctg g                                           21

-continued

```
<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: PCR Primer

<400> SEQUENCE: 38
gccacggcac ctcccccgtg g                                              21

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: PCR Primer

<400> SEQUENCE: 39
ccctctgcaa tgtagggcct gac                                            23

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 40
ccaaggaatg aaccatatgt agcc                                           24

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 41
cagaagagtc aagatgggca ggac                                           24
```

POTASSIUM CHANNELS AND GENES ENCODING THESE POTASSIUM CHANNELS

This application claims priority on provisional Application No. 60/118,112 filed on Feb. 1, 1999, the entire contents of which are hereby incorporated by reference.

TECHNICAL FIELD

This invention relates to novel potassium channels and genes encoding these channels. More specifically the invention provides isolated polynucleotides encoding the KCNQ4 potassium channel subunit, cells transformed with these polynucleotides, transgenic animals comprising genetic mutations, and the use of the transformed cells and the transgenic animals for the in vitro and in vivo screening of chemical compounds affecting KCNQ4 subunit containing potassium channels.

BACKGROUND ART

Potassium channels participate in the regulation of electrical signalling in excitable cells, and regulates the ionic composition of biological fluids. Mutations in the three known genes of the KCNQ branch of the $K^+$-channel gene family underlie inherited cardiac arrhythmia's, in some cases associated with deafness, and neonatal epilepsy.

Hearing loss is the most frequent sensory defect in humans. Hearing loss can be due to environmental and genetic factors, and the progressive hearing loss of the elderly (presbyacusis) most often seems to be due to a combination of both.

Inherited deafness can be classified as non-syndromic (isolated hearing loss) or syndromic (associated with other anomalies). Several hundred syndromes, consisting of hearing loss associated with defects in a variety of other organ systems, have been described. Non-syndromic deafness is classified according to its mode of inheritance as DFN, DFNA, and DFNB (X-linked, autosomal dominant and autosomal recessive, respectively). In general, autosomal recessive deafness has an early onset and is very severe. Autosomal dominant deafness, by contrast, more often develops slowly over several decades and may become apparent only in adulthood. It is hoped that genes identified in families with dominant deafness may also—with different types of mutations—underlie some forms of presbyacusis.

A bewildering number of loci for non-syndromic deafness were identified in the last four years. There are at least 19 loci for autosomal dominant deafness (DFNA1 to DFNA19), and 22 loci for DFNB. Sometimes, depending on the particular mutation, the same gene can be involved in dominant or recessive deafness. This large number of loci reflects the complexity of the inner ear. Identification of these genes and characterisation of their products will significantly advance our understanding of the molecular basis of the physiology of this sensory organ.

Several genes involved in syndromic and non-syndromic deafness have already been identified and are reviewed by Petit [Petit C: Genes responsible for human hereditary deafness: symphony of a thousand; *Nature Genet.* 1996 14 385–391] and Kalatzis & Petit [Kalatzis V & Petit C: The fundamental and medical impacts of recent progress in research on hereditary hearing loss; *Hum. Mol. Genet.* 1998 7 1589–1597]. Among others, their gene products include transcription factors, unconventional myosin isoforms, α-tectorin (an extracellular matrix protein), diaphanous, a protein interacting with the cytoskeleton, connexin 26 (a gap junction protein), and two genes encoding potassium channel subunits, KCNQ1 and KCNE1.

Ion channels play important roles in signal transduction and in the regulation of the ionic composition of intra- and extracellular fluids. Mutations in ion channels were since long suspected as possibly underlying some forms of hearing loss. In the cochlea (the auditory sensory organ), the transduction current through the sensory cells is carried by potassium ions and depends on the high concentration of that ion in the endolymph. So far only two genes encoding potassium channel subunits, KCNQ1 and KCNE1, were found to be mutated in syndromic hereditary deafness. The gene products of both genes, the KCNQ1 (or KvLQT1) and the minK (or IsK) protein, respectively, form heteromeric potassium channels.

KCNQ1 is a typical member of the voltage-gated potassium channel superfamily with 6 transmembrane domains and a pore region situated between the fifth and the sixth transmembrane domain. The minK protein has a single transmembrane span and cannot form potassium channels on its own. However, as a β-subunit it enhances and modifies currents mediated by KCNQ1. These heteromeric channels participate in the repolarization of the heart action potential. Certain mutations in either KCNQ1 or KCNE1 cause a form of the autosomal dominant long QT syndrome (LQTS), a disease characterised by repolarization anomalies of cardiac action potentials resulting in arrhythmias and sudden death. Interestingly, other mutations in either gene lead to the recessive Jervell and Lange-Nielsen (JLN) syndrome that combines LQTS with congenital deafness. In order to cause deafness, KCNQ1/minK currents must be reduced below levels that are already sufficiently low to cause cardiac arrhythmia.

SUMMARY OF THE INVENTION

We have now cloned and characterised KCNQ4, a novel member of the KCNQ family of potassium channel proteins. KCNQ4 has been mapped to the DFNA2 locus for autosomal dominant hearing loss, and a dominant negative KCNQ4 mutation that causes deafness in a DFNA2 pedigree was identified.

KCNQ4 is the first potassium channel gene underlying non-syndromic deafness. KCNQ4 forms heteromeric channels with other KCNQ channel subunits, in particular KCNQ3.

The present invention has important implications for the characterisation and exploitation of this interesting branch of the potassium channel super family, as well as for the understanding of the cochlear physiology, and for human deafness and progressive hearing loss.

Accordingly, in its first aspect, the invention provides an isolated polynucleotide having a nucleic acid sequence which is capable of hybridising under high stringency conditions with the polynucleotide sequence presented as SEQ ID NO: 1, its complementary strand, or a sub-sequence thereof.

In another aspect the invention provides a recombinantly produced polypeptide encoded by the .polynucleotide of the invention.

In a third aspect the invention provides a cell genetically manipulated by the incorporation of a heterologous polynucleotide of the invention.

In a fourth aspect the invention provides a method of screening a chemical compound for inhibiting or activating or otherwise modulating the activity on a potassium channel comprising at least one KCNQ4 channel subunit, which method comprises the steps of subjecting a KCNQ4 channel subunit containing cell to the action of the chemical compound; and monitoring the membrane potential, the current, the potassium flux, or the secondary calcium influx of the KCNQ4 channel subunit containing cell.

In a fifth aspect the invention relates to the use of a polynucleotide sequence of the invention for the screening of genetic materials from humans suffering from loss of hearing (e.g. dominant, recessive, or otherwise), tinnitus, and other neurological diseases for mutations in the KCNQ4 gene.

In a sixth aspect the invention relates to the chemical compound identified by the method of the invention, in particular to the use of such compounds for diagnosis, treatment or alleviation of a disease related to tinnitus; loss of hearing, in particular progressive hearing loss, neonatal deafness, and presbyacusis (deafness of the elderly); and diseases or adverse conditions of the CNS, including affective disorders, Alzheimer's disease, anxiety, ataxia, CNS damage caused by trauma, stroke or neurodegenerative illness, cognitive deficits, compulsive behaviour, dementia, depression, Huntington's disease, mania, memory impairment, memory disorders, memory dysfunction, motion disorders, motor disorders, neurodegenerative diseases, Parkinson's disease and Parkinson-like motor disorders, phobias, Pick's disease, psychosis, schizophrenia, spinal cord damage, stroke, and tremor.

In a seventh aspect the invention provides a transgenic animal comprising a knock-out mutation of the endogenous KCNQ4 gene, a replacement by or an additional expression of a mutated KCNQ4 gene, or genetically manipulated in order to over-express the KCNQ4 gene or to over-express mutated KCNQ4 gene.

In an eighth aspect the invention relates to the use of the transgenic animal of the invention for the in vivo screening of therapeutic compounds.

Other objects of the invention will be apparent to the person skilled in the art from the following detailed description and examples.

DETAILED DISCLOSURE OF THE INVENTION

The present invention provides novel voltage-gated potassium channels and genes encoding these channels. The invention also provides cells transformed with these genes, transgenic animals comprising genetic mutations, and the use of the transformed cells and the transgenic animals for the in vitro and in vivo screening of drugs affecting KCNQ4 containing potassium channels.

Polynucleotides

In its first aspect, the invention provides novel polynucleotides.

The polynucleotides of the invention are such which have a nucleic acid sequence capable of hybridising under high stringency conditions with the polynucleotide sequence presented as SEQ ID NO: 1, its complementary strand, or a sub-sequence thereof.

The polynucleotides of the invention include DNA, cDNA and RNA sequences, as well as anti-sense sequences, and include naturally occurring, synthetic, and intentionally manipulated polynucleotides. The polynucleotides of the invention also include sequences that are degenerate as a result of the genetic code.

As defined herein, the term "polynucleotide" refers to a polymeric form of nucleotides of at least 10 bases in length, preferably at least 15 bases in length. By "isolated polynucleotide" is meant a polynucleotide that is not immediately contiguous with both of the coding sequences with which it is immediately contiguous (one on the 5' end and one on the 3' end) in the naturally occurring genome of the organism from which it is derived. The term therefore includes recombinant DNA which is incorporated into an expression vector, into an autonomously replicating plasmid or virus, or into the genomic DNA of a prokaryote or eukaryote, or which exists as a separate molecule, e.g. a cDNA, independent from other sequences.

The polynucleotides of the invention also include allelic variants and "mutated polynucleotides" comprising a nucleotide sequence that differs from the sequence presented as SEQ ID NO: 1 at one or more nucleotide positions. The mutated polynucleotide may in particular be a polynucleotide of the invention comprising a nucleotide sequence as in SEQ ID NO: 1, which sequence, however, differs from SEQ ID NO: 1 so as to effect the expression of a variant polypeptide. The mutated polynucleotide may be a polynucleotide of the invention having a nucleotide sequence encoding a potassium channel having an amino acid sequence that has been changed at one or more positions. The mutated polynucleotide may in particular be a polynucleotide of the invention having a nucleotide sequence encoding a potassium channel having an amino acid sequence that has been changed at one or more positions located in the conserved regions, as defined by Table 1, below.

In a more specific embodiment the polynucleotide of the invention has the polynucleotide sequence giving rise to the G285S mutation as indicated in SEQ ID NO: 1, i.e. the DNA sequence that at position 935–937 holds the codon AGC rather than the codon GGC stated in SEQ ID NO: 1.

Hybridisation Protocol

The polynucleotides of the invention are such which have a nucleic acid sequence capable of hybridising with the polynucleotide sequence presented as SEQ ID NO: 1, its complementary strand, or a sub-sequence thereof, under at least medium, medium/high, or high stringency conditions, as described in more detail below.

In a preferred embodiment the polynucleotide is a fragment of at least 15 bases in length which is sufficient to permit the fragment to hybridise to DNA that encodes a polypeptide of the invention, preferably the polypeptide comprising the amino acid sequence presented as SEQ ID NO: 2 under at least medium, medium/high, or high stringency conditions, as described in more detail below.

Suitable experimental conditions for determining hybridisation between a nucleotide probe and a homologous DNA or RNA sequence, involves pre-soaking of the filter containing the DNA fragments or RNA to hybridise in 5×SSC [Sodium chloride/Sodium citrate; cf. Sambrook et al.; *Molecular Cloning: A Laboratory Manual,* Cold Spring Harbor Lab., Cold Spring Harbor, N.Y. 1989] for 10 minutes, and pre-hybridisation of the filter in a solution of 5×SSC, 5×Denhardt's solution [cf. Sambrook et al.; Op cit.], 0.5% SDS and 100 µg/ml of denatured sonicated salmon sperm DNA [cf. Sambrook et al.; Op cit.], followed by hybridisation in the same solution containing a concentration of 10 ng/ml of a random-primed [Feinberg A P & Vogelstein B; *Anal. Biochem.* 1983 132 6–13], $^{32}$PdCTP-labeled (specific activity>1×10$^9$ cpm/µg) probe for 12 hours at approximately 45° C. The filter is then washed twice for 30 minutes in 2×SSC, 0.5% SDS at a temperature of at least at least 60° C. (medium stringency conditions), preferably of at least 65° C. (medium/high stringency conditions), more preferred of at least 70° C. (high stringency conditions), and even more preferred of at least 75° C. (very high stringency conditions).

Molecules to which the oligonucleotide probe hybridises under these conditions may be detected using a x-ray film.

DNA Sequence Homology

In a preferred embodiment, the polynucleotides of the invention show a homology of at least 50%, preferably at least 70%, more preferred at least 80%, even more preferred at least 90%, most preferred at least 95%, with the polynucleotide sequence presented as SEQ ID NO: 1.

As defined herein, the DNA sequence homology may be determined as the degree of identity between two DNA sequences indicating a derivation of the first sequence from the second. The homology may suitably be determined by means of computer programs known in the art such as GAP provided in the GCG program package [Needleman S B and Wunsch C D, *Journal of Molecular Biology* 1970 48 443–453] using default para meters suggested herein.

Cloned Polynucleotides

The isolated polynucleotide of the invention may in particular be a cloned polynucleotide.

As defined herein, the term "cloned polynucleotide", refers to a polynucleotide or DNA sequence cloned in accordance with standard cloning procedures currently used in genetic engineering to relocate a segment of DNA, which may in particular be cDNA, i.e. enzymatically derived from RNA, from its natural location to a different site where it will be reproduced.

Cloning may be accomplished by excision and isolation of the desired DNA segment, insertion of the piece of DNA into the vector molecule and incorporation of the recombinant vector into a cell where multiple copies or clones of the DNA segment will be replicated, by reverse transcription of mRNA (reverse transcriptase technology), and by use of sequence-specific oligonucleotides and DNA polymerase in a polymerase chain reaction (PCR technology).

The cloned polynucleotide of the invention may alternatively be termed "DNA construct" or "isolated DNA sequence", and may in particular be a complementary DNA (cDNA).

It is well established that potassium channels may be formed as heteromeric channels, composed of different subunits. Also it has been found that the potassium channel of the invention may form heteromers with other KCNQ's, in particular KCNQ3. when co-expressed with these subunits. In addition, potassium channels can also associate with non-homologous subunits, e.g. the KCNE1 (formerly known as minK) subunit, that can functionally modulate these channels or lead to a specific localisation within the cell.

Therefore, in a preferred embodiment, the polynucleotide of the invention is cloned and either expressed by itself or co-expressed with polynucleotides encoding other subunits, in particular a polynucleotide encoding a KCNQ3 channel subunit.

Biological Sources

The isolated polynucleotide of the invention may be obtained from any suitable source. In a preferred embodiment, which the polynucleotide of the invention is cloned from, or produced, on the basis of a cDNA library, e.g. of the retina, brain, skeletal muscle. Commercial cDNA libraries are available from e.g. Stratagene and Clontech.

The isolated polynucleotide of the invention may be obtained by methods known in the art, e.g. those described in the working examples below.

In a preferred embodiment the polynucleotide of the invention may be obtained using the PCR primers described in the working examples and presented as SEQ ID NOS: 3–32.

Preferred Polynucleotides

In a preferred embodiment, polynucleotide of the invention comprises the polynucleotide sequence presented as SEQ ID NO: 1.

In another preferred embodiment the polynucleotide of the invention is a sequence giving rise to KCNQ4 channels subunits comprising one or more substitutions.

In another preferred embodiment the polynucleotide of the invention is a sequence giving rise to KCNQ4 channels subunits comprising one or more substitutions in the conserved regions, as defined in more details below.

In a more preferred embodiment the polynucleotide of the invention has a polynucleotide sequence giving rise to the G285S mutation as indicated in SEQ ID NO: 1, e.g. the DNA sequence that at position 935–937 holds the codon AGC rather than the codon GGC stated in SEQ ID NO: 1.

Also contemplated within the scope of this invention are the primer sequences used in Example 2 below for the amplification of the single KCNQ4 exons, that can then be screened for mutations.

Therefore, in another preferred embodiment the polynucleotide of the invention is a primer sequence comprising any one of the polynucleotide sequences presented as SEQ ID NOS: 3–32.

It has been demonstrated that KCNQ channels often show alternative splicing and therefore may occur as isoforms originating from the same gene. Such isoforms as well as the different cDNA sequences from which they occurred are also contemplated within the scope of the present invention.

Finally the genes encoding KCNQ channel subunits in other species have been found to differ slightly from the human genes. However, genes of other species, e.g. mouse, rat, monkey, rabbit, etc., are also contemplated within the scope of the present invention.

Recombinantly Produced Polypeptides

In another aspect the invention relates to substantially pure functional polypeptides that have the electrophysiological and pharmacological properties of a KCNQ4 channel, or KCNQ4 channel subunits. The novel polypeptides of the invention may be obtained by the polynucleotides of the invention using standard recombinant DNA technology.

In a preferred embodiment, a polypeptide of the invention is the KCNQ4 potassium channel subunit comprising the amino acid sequence presented as SEQ ID NO: 2, and biologically active fragments hereof.

Modifications of this primary amino acid sequence may result in proteins which have substantially equivalent activity as compared to the unmodified counterpart polypeptide, and thus may be considered functional analogous of the parent proteins. Such modifications may be deliberate, e.g. as by site-directed mutagenesis, or they may occur spontaneous, and include splice variants, isoforms, homologues from other species, and polymorphisms, and include the variant KCNQ4/G285S, that is described in more detail below. Such functional analogous are also contemplated according to the invention.

Moreover, modifications of this primary amino acid sequence may result in proteins which do not retain the biological activity of the parent protein, including dominant negative forms, etc. A dominant negative protein may interfere with the wild-type protein by binding to, or otherwise sequestering regulating agents, such as upstream or downstream components, that normally interact functionally with the polypeptide. Such dominant negative forms are also contemplated according to the invention.

In the context of this invention, the term "variant polypeptide" means a polypeptide (or protein) having an amino acid sequence that differs from the sequence presented as SEQ ID NO; 2 at one or more amino acid positions. Such variant polypeptides include the modified polypeptides described above, as well as conservative substitutions, splice variants, isoforms, homologues from other species, and polymorphisms, and includes the variant KCNQ4/G285S (i.e. KCNQ4/G333S according to the KCNQ1 numbering).

As defined herein, the term "conservative substitutions" denotes the replacement of an amino acid residue by another, biologically similar residue. Examples of conservative substitutions include the substitution of one hydrophobic residue such as isoleucine, valine, leucine or methionine for another, or the substitution of one polar residue for another, such as, the substitution of arginine for lysine, glutamic for aspartic acid, or glutamine for asparagine, and the like. The term conservative substitution also include the use of a substituted amino acid residue in place of an un-substituted parent amino acid residue provided that antibodies raised to the substituted polypeptide also immunoreact with the un-substituted polypeptide.

Also contemplated within the scope of this invention are the oligopeptides encoded by the primer sequences used in Example 2 below for the amplification of the single KCNQ4 exons, that can then be screened for mutations.

KCNQ1 Numbering System

In the context of this invention, amino acid residues (as well as nucleic acid bases) are specified using the established one-letter symbol.

By aligning the amino acid sequences of a polypeptide of the present invention to those of the known polypeptides, a specific amino acid numbering system may be employed, by which,system it is possible to unambiguously allot an amino acid position number to any amino acid residue in any KNCQ channel protein, which amino acid sequence is known.

Such an alignment is presented in Table 1, below. Using the ClustalX computer alignment program [Thompson J D, Gibson T J, Plewniak F, Jeanmougin F, & Higgins D G: The ClustalX windows interface: flexible strategies for multiple sequence alignment aided by quality analysis tools; *Nucleic Acids Res.* 1997 25 (24) 4876–82], and the default parameters suggested herein, the amino acid sequence of a polypeptide of the present invention (hKCNQ4) and the amino acid sequences of the known polypeptides hKCNQ2–3 are; aligned with, and relative to, the amino acid sequences of the known polypeptide hKCNQ1 (formerly known as KvLQT1). In the context of this invention this numbering system is designated the KCNQ1 Numbering System.

In describing the various protein variants produced or contemplated according to the invention, the following nomenclatures have been adapted for ease of reference:

Original Amino Acid/Position/Substituted Amino Acid

According to this nomenclature the substitution of serine for glycine at position 333 is designated as "G333S".

A deletion of glycine at the same position is designated "G333*".

An insertion of an additional amino acid residue, in this example lysine, may be designated "G333GK" or "*334K" (assumed that no position exists for this position in the amino acid sequence used for establishing the numbering system).

An insertion of an amino acid residue, in this example valine, at a position which exists in the established numbering system, but where no amino acid residue is actually present, may be designated "–301V".

TABLE 1

CLUSTAL X Multiple Sequence Alignment

KCNQ1 Numbering

```
hKCNQ2 MVQKSR----  ----------  NGGVYPGPSG  EKKLKVG---  -FVGLDPG--  -------APD        60 hKCNQ3 MGLKARRAAG  AAGGGGDGGG  GGGGAANPAG  GDAAAAGDEE  RKVGLAPGDV  EQVTLALGAG hKCNQ4 MAEAPPR---  ----------  RLGLGPPPGD  APRAELVALT  -AVQSEQGE-  -------AGG hKCNQ1 MAAASSPPR-  -AE--RKR-W  GWGRLPGARR  GSAGLAKKCP  FSLELAEG--  -------GPA
        *    .                 *   . .                 :    *              .

hKCNQ2 STRDGALLIA  G--------S  EAPKRGSILS  KPRAGGAGAG  KPPKRN-AFY  RK-------L       120 hKCNQ3 ADKDGTLLLE  GGG------R  DEGQRRTPQG  IGLLAKTPLS  RPVKRNNAKY  RR-------I hKCNQ4 GGSPRRLGLL  G--------S  PLPPGAPLPG  PGSGSGSACG  QRSSAAHKRY  RR-------L hKCNQ1 GGALYAPIAP  GAPGPAPPAS  PAAPAAPPVA  SDLGPRPPVS  LDPRVSIYST  RRPVLARTHV
                       *                  . .         . .              *:        :

hKCNQ2 QNFLYNVLER  PRGW-AFIYH  AYVFLLVFSC  LVLSVFSTIK  EYEKSSEGAL  YILEIVTIVV      180 hKCNQ3 QTLIYDALER  PRGW-ALLYH  ALVFLIVLGC  LILAVLTTFK  EYETVSGDWL  LLLETFAIFI hKCNQ4 QNWVYNVLER  PRGW-AFVYH  VFIFLLVFSC  LVLSVLSTIQ  EHQELANECL  LILEFVMIVV hKCNQ1 QGRVYNFLER  PTGWKCFVYH  FAVFLIVLVC  LIFSVLSTIE  QYAALATGTL  FWMEIVLVVF
         *   :*: ***  *   .: *       :**:*:  *  *:::*::*::  ::      :   *    :* .  :..
```

TABLE 1-continued

CLUSTAL X Multiple Sequence Alignment

KCNQ1 Numbering

| | | | | | | |
|---|---|---|---|---|---|---|
| hKCNQ2 | FGVEYFVRIW | AAGCCCRYRG | WRGRLKFARK | PFCVIDIMVL | IASIAVLAAG | SQGNVFATSA | 240 |
| hKCNQ3 | FGAEFALRIW | AAGCCCRYKG | WRGRLKFARK | PLCMLDIFVL | IASVPVVAVG | NQGNVLATS- | |
| hKCNQ4 | FGLEYIVRVW | SAGCCCRYRG | WQGRFRFARK | PFCVIDFIVF | VASVAVIAAG | TQGNIFATSA | |
| hKCNQ1 | FGTEYVVRLW | SAGCRSKYVG | LWGRLRFARK | PISIIDLIVV | VASMVVLCVG | SKGQVFATSA | |
| | ** *: :*:* | :*** ..:* * | ::** | *:..:*::*. | :**: *:..* | ..:*:::*** | |
| hKCNQ2 | LRSLRFLQIL | RMIRMDRRGG | TWKLLGSVVY | AHSKELVTAW | YIGFLCLILA | SFLVYLAEK- | 300 |
| hKCNQ3 | LRSLRFLQIL | RMLRMDRRGG | TWKLLGSAIC | AHSKELITAW | YIGFLTLILS | SFLVYLVEKD | |
| hKCNQ4 | LRSMRFLQIL | RMVRMDRRGG | TWKLLGSVVY | AHSKELITAW | YIGFLVLIFA | SFLVYLAEKD | |
| hKCNQ1 | IRGIRFLQIL | RMLHVDRQGG | TWRLLGSVVF | IHRQELITTL | YIGFLGLIFS | SYFVYLAEKD | |
| | :*..:**** | ::: | :**.: | * :**:*: | *** :: | *::*. | |
| hKCNQ2 | -------GE- | -NDHFDTYAD | ALWWGLITLT | TIGYGDKYPQ | TWNGRLLAAT | FTLIGVSFFA | 360 |
| hKCNQ3 | VPEVDAQGEE | MKEEFETYAD | ALWWGLITLA | TIGYGDKTPK | TWEGRLIAAT | FSLIGVSFFA | |
| hKCNQ4 | ---------- | ANSDFSSYAD | SLWWGTITLT | TIGYGDKTPH | TWLGRVLAAG | FALLGISFFA | |
| hKCNQ1 | -----AVNES | GRVEFGSYAD | ALWWGVVTVT | TIGYGDKVPQ | TWVGKTIASC | FSVFAISFFA | |
| | . .* :*** | :**** :*:: | ******* *: | ** *: :*: | *:::..:**** | | |
| hKCNQ2 | LPAGILGSGF | ALKVQEQHRQ | KHFEKRRNPA | AGLIQSAWRF | YATNLSRTDL | HSTWQYYERT | 420 |
| hKCNQ3 | LPAGILGSGL | ALKVQEQHRQ | KHFEKRRKPA | AELIQAAWRY | YATNPNRIDL | VATWRFYESV | |
| hKCNQ4 | LPAGILGSGF | ALKVQEQHRQ | KHFEKRRMPA | ANLIQAAWRL | YSTDMSRAYL | TATWYYYDSI | |
| hKCNQ1 | LPAGILGSGF | ALKVQQKQRQ | KHFNRQIPAA | ASLIQTAWRC | YAAE--NPD- | SSTWKIYIRK | |
| | ******* | *:: | *::: | .* * *:* | *::: . | :** * | |
| hKCNQ2 | VT-------- | VPMYRLIPP- | -LNQLELLRN | LKSKSGLAFR | K--------- | DPPPEPSPSQ | 480 |
| hKCNQ3 | VS-------- | FPFFRKE--- | ---QLEAAS- | ---------- | ---------- | ------S--Q | |
| hKCNQ4 | LPSFRELALL | FEHVQRARNG | GLRPLEVRRA | PVPDGAPSRY | PPVATCHRPG | STSFCPGESS | |
| hKCNQ1 | AP-------- | RSHTLLS--- | ---PSPKPKK | ---------- | ---------- | ---------S | |
| | | . | | | | . | |
| hKCNQ2 | KVSLKDRV-F | SSPRGVAAKG | KGSPQAQTVR | RSPSADQSLE | D-SPSKVPKSW | SFG-DRSRA | 540 |
| hKCNQ3 | KLGLLDRVRL | SNPRGSNTKG | K--------L | FTPLNVDAIE | E-SPSKEPKPV | GLN-NKERF | |
| hKCNQ4 | RMGIKDRIRM | GSSQRRTGPS | KQQLAPPTMP | TSPSSEQVGE | ATSPTKVQKSW | SFN-DRTRF | |
| hKCNQ1 | VVVKKKKFKL | DKDNGVTPGE | K-MLTVPHIT | CDPPEERRLD | HFSVDGYDSSV | RKSPTLLEV | |
| | : .:.: :... . | * | * | : * | .. | . . | |
| hKCNQ2 | RQAFRIKGAA | SRQNSEEASL | PGEDIVDDKS | CPCEFVTEDL | TPGLKVSIRA | VCVMRFLVSK | 600 |
| hKCNQ3 | RTAFRMKAYA | FWQSSEDAGT | -GDPMAEDRG | YGNDFPIEDM | IPTLKAAIRA | VRILQFRLYK | |
| hKCNQ4 | RASLRLKP-- | -RTSAEDAPS | --EEVAEEKS | YQCELTVDDI | MPAVKTVIRS | IRILKFLVAK | |
| hKCNQ1 | SMPHFMRT-- | -NSFAEDLDL | EGETLLTPIT | H-----ISQL | REHHRATIKV | IRRMQYFVAK | |
| | . :: | :*: | : : | .:: | :. *: : | ::: : * | |
| hKCNQ2 | RKFKESLRPY | DVMDVIEQYS | AGHLDMLSRI | KSLQSRVDQI | VGRGP----A | ITDKDR-TK | 660 |
| hKCNQ3 | KKFKETLRPY | DVKDVIEQYS | AGHLDMLSRI | KYLQTRIDMI | FTPGP----P | STPKHKKSQK | |
| hKCNQ4 | RKFKETLRPY | DVKDVIEQYS | AGHLDMLGRI | KSLQTRVDQI | VGRGP----G | DRKAREKGDK | |
| hKCNQ1 | KKFQQARKPY | DVRDVIEQYS | QGHLNLMVRI | KELQRRLDQS | IGK-PSLFIS | VSEKSK--DR | |
| | :**: : |  ** | *::: ** | * ** *:* | . * | . : | |

TABLE 1-continued

CLUSTAL X Multiple Sequence Alignment

KCNQ1 Numbering

| | | | | | | |
|---|---|---|---|---|---|---|
| hKCNQ2 | G--------- | ---------- | PAEAELPEDP | SMMGRLGKVE | KQVLSMEKKL | DFLVNIY--M | 720 |
| hKCNQ3 | GSAFTFPSQQ | SPRNEPYVAR | PSTSEI-EDQ | SMMGKFVKVE | RQVQDMGKKL | DFLVDMH--M | |
| hKCNQ4 | G--------- | ---------- | PSDAEVVDEI | SMMGRVVKVE | KQVQSIEHKL | DLLLGFYSRC | |
| hKCNQ1 | G--------- | ---------- | --------SN | TIGARLNRVE | DKVTQLDQRL | ALITDML--- | |
| | * | | . :: .:. :** | :* .: ::* | :: .: | | |
| hKCNQ2 | QRMGIPPTET | EAYFGAKEPE | PAPPYHSPED | SREHVDRHGC | IVKIVRSSSS | TGQKNF---S | 780 |
| hKCNQ3 | QHMERLQVQV | TEYYPTKGTS | SPAEAEKKED | NR-YSDLKTI | ICNYSETGPP | EPPYSFHQVT | |
| hKCNQ4 | LRSGTSASLG | AVQVPLFDPD | ITSDYHSPVD | HE-DISVSAQ | TLSISRSVST | NMD------- | |
| hKCNQ1 | -HQLLSLHGG | STP-GSGGPP | REGGAHITQP | CGSGGSVDPE | LFLPSNTLPT | YEQLTV---- | |
| | : | | . | . | . | .: .. | |
| hKCNQ2 | APPAAPPVQC | PPSTSWQPQS | HPRQG--HGT | SPVGDHGSLV | RIPPPPAHER | SLSAYGGGNR | 840 |
| hKCNQ3 | IDKVSPYGFF | AHDPVNLPRG | GPSSGKVQAT | PPSSATTYVE | RPTVLPILTL | LDSRVSCHSQ | |
| hKCNQ4 | ---------- | ---------- | ---------- | ---------- | ---------- | ---------- | |
| hKCNQ1 | PRRGPDEGS- | ---------- | ---------- | ---------- | ---------- | ---------- | |
| hKCNQ2 | ASMEFLRQED | TPGCRPPEGT | LRDSDTSISI | PSVDHEELER | SFSGFSISQS | KENLDALNSC | 900 |
| hKCNQ3 | ADLQGP-YSD | RISPRQRRSI | TRDSDTPLSL | MSVNHEELER | SPSGFSISQD | RD--DYVFGP | |
| hKCNQ4 | ---------- | ---------- | ---------- | ---------- | ---------- | ---------- | |
| hKCNQ1 | ---------- | ---------- | ---------- | ---------- | ---------- | ---------- | |
| hKCNQ2 | YAAVAPCAKV | RPYIAEGESD | TDSDLCTPCG | PPPRSATGEG | PFGDVGWAGP | RK-- | 954 |
| hKCNQ3 | NGGSSWMREK | R-YLAEGETD | TDTDPFTPSG | SMPLSSTGDG | -ISDSVWTPS | NKPI | |
| hKCNQ4 | ---------- | ---------- | ---------- | ---------- | ---------- | ---- | |
| hKCNQ1 | ---------- | ---------- | ---------- | ---------- | ---------- | ---- | | hKCNQ1: Human KCNQ1 (SEQ ID NO:33) [Wang, Q et al., Nature Genet. 1996 12 17–23]
hKCNQ2: Human KCNQ2 (SEQ ID NO:34) [Biervert et al., Science 1998 279 403–406]
hKCNQ3: Human KCNQ3 (SEQ ID NO:35) [Schroeder et al., Nature 1998 396 687–690]
hKCNQ4: Human KCNQ4 (SEQ ID NO:2); A protein of the invention
- No amino acid in this position
* Indicates positions which have a single, fully conserved residue (Conserved regions).

Biological Activity

The polynucleotide of the invention encodes a potassium channel subunit, which has been termed KNCQ4. In the cochlea, it is differentially expressed in sensory outer hair cells. A mutation in this gene in a pedigree with autosomal dominant hearing loss changes a residue in the KCNQ4 pore region. It abolishes the outwardly rectifying potassium currents of wild-type KCNQ4 on which it exerts a strong dominant negative effect.

Ion channels are excellent targets for drugs. KCNQ4, or heteromeric channels containing the KCNQ4 subunit, may be a particularly interesting target for the treatment of tinnitus and the prevention or treatment of progressive hearing loss.

KCNQ Channels in Genetic Disease

It is remarkable that mutations in every known KCNQ gene lead to human disease: Mutations in KCNQ1 (KvLQT1) cause the autosomal dominant long QT syndrome (LQTS), and, when present on both alleles, the Jervell and Lange-Nielsen (JLN) syndrome whose symptoms include deafness in addition to cardiac arrhythmias. Mutations in either KCNQ2 or KCNQ3, which form heteromers that probably represent the M-channel, cause benign familial neonatal convulsions (BFNC). The present invention adds KCNQ4 and the associated autosomal dominant deafness to that list.

After KCNQ1, KCNQ4 is now the second KCNQ channel whose loss of function leads to deafness.

Therefore, in a preferred embodiment of the invention, mutated polynucleotides may be employed in the screening for drugs that affect diseases associated with such mutations in the KCNQ4 gene.

Heteromers Formed by KCNQ Subunits

The KCNQ channels described so far function physiologically as heteromers. KCNQ1 associates with KCNE1 (formerly known as minK), and KCNQ2 and KCNQ3 form heteromeric channels that underlie the M-current, an important determinant of neuronal excitability that is regulated by several neurotransmitters.

Like other KCNQ channel subunits, KCNQ4 may interact with other subunits, e.g. KCNE1 or other KCNQ channel subunits, and in particular with KCNQ3. Currents from homomeric KCNQ3 are very small and often cannot be distinguished from Xenopus oocyte background currents. Co-expression of KCNQ3 with KCNQ4 markedly increased current amplitudes. Significantly, heteromeric KCNQ3/KCNQ4 channels activated faster than homomeric KCNQ4 channels, the voltage-dependence was shifted to more negative potentials, and currents displayed a different drug sensitivity.

Antibodies

The polypeptides of the invention can be used to produce antibodies which are immunoreactive or bind to epitopes of these polypeptides. Antibodies which consist essentially of pooled monoclonal antibodies with different specificities, as well as distinct monoclonal antibody preparations may be provided.

The preparation of polyclonal and monoclonal antibodies is well known in the art. Polyclonal antibodies may in particular be obtained as described by e.g. Green et al.: "Production of Polyclonal Antisera" in *Immunochemical Protocols* (Manson, Ed.); Humana Press, 1992, Pages 1–5; and Coligan et al.: "Production of Polyclonal Antisera in rabbits, rats, Mice and Hamsters" in *Current Protocols in Immunology*, 1992, Section 2.4.1; which protocols are hereby incorporated by reference.

Monoclonal antibodies may in particular be obtained as described by e.g. Kohler & Milstein, *Nature* 1975 256 495; Coligan et al. in *Current Protocols in Immunology*, 1992, Sections 2.5.1–2.6.7; and Harlow et al. in *Antibodies: A Laboratory Manual*; Cold Spring Harbor Pub., 1988, Page 726; which protocols are hereby incorporated by reference.

Briefly, monoclonal antibodies may be obtained by injecting e.g. mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce the antibodies to the antigen, and isolating the antibodies from the hybridoma cultures.

Monoclonal antibodies can be isolated and purified from hybridoma cultures by a variety of well-established techniques, including affinity chromatography with protein A Sepharose, size-exclusion chromatography, and ion-exchange chromatography, see. e.g. Coligan et al. in *Current Protocols in Immunology*, 1992, Sections 2.7.1–2.7.12, and Sections 2.9.1–2.9.3; and Barnes et al.: "Purification of Immunoglobulin G (IgG)" in Methods in Molecular Biology; Humana Press, 1992, Vol. 10, Pages 79–104.

The polyclonal or monoclonal antibodies may optionally be further purified, e.g. by binding to and elution from a matrix to which the polypeptide, to which the antibodies were raised, is bound.

Antibodies which bind to the polypeptide of the invention can be prepared using an intact polypeptide or fragments containing small peptides of interest as the immunising antigen. The polypeptide used to immunise an animal may be obtained by recombinant DNA techniques or by chemical synthesis, and may optionally be conjugated to a carrier protein. Commonly used carrier proteins which are chemically coupled to the peptide include keyhole limpet hemocyanin (KLH), thyroglobulin, bovine serum albumin (BSA), and tetanus toxoid. The coupled peptide may then be used to immunise the animal, which may in particular be a mouse, a rat, a hamster or a rabbit.

Genetically Manipulated Cells

In a third aspect the invention provides a cell genetically manipulated by the incorporation of the heterologous polynucleotide of the invention. The cell of the invention may in particular be genetically manipulated to transiently or stably express, over-express or co-express a KCNQ4 channel subunit as defined above. Methods of transient and stable transfer are known in the art.

The polynucleotide of the invention may be inserted into an expression vector, e.g. a plasmid, virus or other expression vehicle, and operatively linked to expression control sequences by ligation in a way that expression of the coding sequence is achieved under conditions compatible with the expression control sequences. Suitable expression control sequences include promoters, enhancers, transcription terminators, start codons, splicing signals for introns, and stop codons, all maintained in the correct reading frame of the polynucleotide of the invention so as to permit proper translation of mRNA. Expression control sequences may also include additional components such as leader sequences and fusion partner sequences.

The promoter may in particular be a constitutive or an inducible promoter. When cloning in bacterial systems, inducible promoters such as pL of bacteriophage γ, plac, ptrp, ptac (ptrp-lac hybrid promoter), may be used. When cloning in mammalian systems, promoters derived from the genome of mammalian cells, e.g. the TK promoter or the metallothionein promoter, or from mammalian viruses, e.g. the retrovirus long terminal repeat, the adenovirus late promoter or the vaccinia virus 7.5K promoter, may be used. Promoters obtained by recombinant DNA or synthetic techniques may also be used to provide for transcription of the polynucleotide of the invention.

Suitable expression vectors typically comprise an origin of expression, a promoter as well as specific genes which allow for phenotypic selection of the transformed cells, and include vectors like the T7-based expression vector for expression in bacteria [Rosenberg et al; *Gene* 1987 56 125], the pMSXND expression vector for expression in mammalian cells [Lee and Nathans, *J. Biol. Chem.* 1988 263 3521], baculovirus derived vectors for expression in insect cells, and the oocyte expression vector PTLN [Lorenz C, Pusch M & Jentsch T J: Heteromultimeric CLC chloride channels with novel properties; *Proc. Natl. Acad. Sci. USA* 1996 93 13362–13366].

In a preferred embodiment, the cell of the invention is an eukaryotic cell, in particular a mammalian cell, an oocyte, or a yeast cell. In a more preferred embodiment, the cell of the invention is a human embryonic kidney (HEK) cell, a HEK 293 cell, a BHK21 cell, a Chinese hamster ovary (CHO) cell, a *Xenopus laevis* oocyte (XLO) cell, a COS cell, or, any other cell line able to express KCNQ potassium channels.

When the cell of the invention is an eukaryotic cell, incorporation of the heterologous polynucleotide of the invention may be in particular be carried out by infection (employing a virus vector), by transfection (employing a plasmid vector), or by calcium phosphate precipitation, microinjection, electroporation, lipofection, or other physical-chemical methods known in the art.

In a further preferred embodiment, the cell of the invention is genetically manipulated to co-express KCNQ4 and KCNQ1 channel subunits; KCNQ4 and KCNQ2 channel subunits; KCNQ4 and KCNQ3 channel subunits; KCNQ4 and KCNQ1 and KCNQ2 channel subunits; KCNQ4 and KCNQ1 and KCNQ3 channel subunits; KCNQ4 and KCNQ2 and KCNQ3 channel subunits; or KCNQ4 and KCNO1 and KCNQ2 and KCNQ3 channel subunits.

KCNQ4 Active Chemical Compounds

In another aspect the invention relates to chemical compounds capable of binding to, and showing activity at potassium channels containing one or more KCNQ4 subunits. In the context of this invention such compounds are termed KCNQ4 active compounds. The KCNQ4 active compounds of the invention show activity in concentrations below 100 µM, preferably below 10 µM, more preferred below 1 µm. In its most preferred embodiment the KCNQ4 active compounds of the invention show activity in low micromolar and the nanomolar range.

The KCNQ4 active compounds of the invention have therapeutic potential, and may be used for the manufacture of pharmaceutical compositions.

The KCNQ4 active compounds of the invention may in particular be used in diagnosis, treatment, prevention or alleviation of diseases related to tinnitus, loss of hearing, in particular progressive hearing loss, neonatal deafness, and presbyacusis (deafness of the elderly); and diseases or adverse conditions of the CNS, including affective disorders, Alzheimer's disease, anxiety, ataxia, CNS damage caused by trauma, stroke or neurodegenerative illness, cognitive deficits, compulsive behaviour, dementia, depression, Huntington's disease, mania, memory impairment, memory disorders, memory dysfunction, motion disorders, motor disorders, neurodegenerative diseases, Parkinson's disease and Parkinson-like motor disorders, phobias, Pick's disease, psychosis, schizophrenia, spinal cord damage, stroke, and tremor.

Currently two compound have been identified. As a preferred embodiment the invention therefore provides 1,3-dihydro-1-phenyl-3,3-bis(4-pyridylmethyl)-2H-indol-2-one (Linopirdine) and 10,10-bis(4-pyridinyl-methyl)-9(10H)-antracenone (XE991) for use in the manufacture of a pharmaceutical composition for the diagnosis, treatment, prevention or alleviation of the above diseases.

Screening of Drugs

In a further aspect the invention provides methods for screening for KCNQ4 active compounds, i.e. chemical compounds capable of binding to, and showing activity at potassium channels containing one or more KCNQ4 subunits. The activity determined may be inhibitory activity, stimulating activity, or other modulatory activity. In particular the KCNQ4 active compound may induce a second messenger response, which cause a change of the molecular characteristics of the cell, e.g. the ion flux, enzyme activation, changes in cyclic nucleotides such as cAMP, cADP, cGMP, and cGDP, etc.

Therefore, in another aspect, the invention provides a method for identifying functional ligands for a human potassium channel, comprising a KCNQ4 subunit, which method comprises transfecting cells with one or more polypeptides of the invention, encoding a KCNQ4 channel subunit, and detecting the effect on the signal transduction pathway caused in these cells by binding of the ligands to the receptor by a reporter system.

Such chemical compounds can be identified by one of, or both methods described below.

Binding Studies

Binding studies are usually carried out by subjecting the target to binding with a labelled, selective agonist (binding agent), to form a labelled complex, followed by determination of the degree of displacement caused by the test compound upon addition to the complex.

In a specific aspect the invention provides a method of screening a chemical compound for capability of binding to a potassium channel comprising at least one KCNQ4 channel subunit, which method comprises the steps of (i) subjecting a KCNQ4 channel subunit containing cell to the action of a KCNQ4 binding agent to form a complex with the KCNQ4 channel subunit containing cell; (ii) subjecting the complex of step (i) to the action of the chemical compound to be tested; and (iii) detecting the displacement of the KCNQ4 binding agent from the complex with the KCNQ4 channel subunit containing cell.

The KCNQ4 channel subunit containing cell preferably is a cell of the invention as described above.

The KCNQ4 binding agent preferably is a radioactively labelled 1,3-dihydro-1-phenyl-3,3-bis(4-pyridylmethyl)-2H-indol-2-one (Linopirdine); or 10,10-bis(4-pyridinyl-methyl)-9(10H)-antracenone.

In a even more preferred embodiment, the biding agent is labelled with $^3H$, and the displacement of the KCNQ4 binding agent from the complex with the KCNQ4 channel subunit containing cell is detected by measuring the amount of radioactivity by conventional liquid scintillation counting.

Activity Studies

The KCNQ4 channel agonists may affect the potassium channel in various ways. The agonist may in particular show inhibitory activity, stimulating activity, or other modulatory activity.

In a specific aspect the invention provides a method for determining the activity at potassium channels containing one or more KCNQ4 subunits. According to this method a KCNQ4 channel subunit containing cell is subjecting to the action of the chemical compound to be tested, and the activity is detected by way of monitoring the membrane potential, the current, the potassium flux, or the secondary calcium influx of the KCNQ4 channel subunit containing cell, preferably a genetically manipulated as described above.

The membrane potential and the current may be monitored by electrophysiologic methods, including patch clamp techniques, such as current clamp technology and two-electrode voltage clamp technology, or by spectroscopic methods, such as fluorescence methods.

In a preferred embodiment, monitoring of the membrane potential of the KCNQ4 channel subunit containing cell is performed by patch clamp techniques.

In another preferred embodiment, monitoring of the membrane potential of the KCNQ4 channel subunit containing cell is performed by spectroscopic methods, e.g. using fluorescence methods. In a more specific embodiment, the KCNQ4 channel subunit containing cell is mixed with a membrane potential indicating agent, that allow for a determination of changes in the membrane potential of the cell, caused by the addition of the test compound. The membrane potential indicating agent may in particular be a fluorescent indicator, preferably $DIBAC_4(3)$, DiOC5(3), and DiOC2(3).

In yet a preferred embodiment, monitoring of the membrane potential of the KCNQ4 channel subunit containing cell is performed by spectroscopic methods, e.g. using a FLIPR assay (Fluorescence Image Plate Reader; available from Molecular Devices).

Screening of Genetic Material

In a further aspect the invention relates to the use of a polynucleotide sequence of the invention for the screening of genetic materials. By this method, individuals bearing a gene identical or homologous to a polynucleotide of the invention may be identified.

In the screening method of the invention, a polynucleotide of the invention, or any fragment or sub-sequence hereof, and in particular any one of the polynucleotide sequences presented as SEQ ID NOS: 3–32, is employed. For the identification of individuals bearing mutated genes, preferably a mutated form of the polynucleotide represented by SEQ ID NO: 1 is employed, and in particular a polynucleotide sequence holding the mutation giving rise to the KCNQ4/G285S variant.

In the screening method of the invention only short sequences needs to be employed depending on the actual method used. For SSCA, several hundreds of base pairs may be needed, for oligonucleotide or PCR hybridisation only of from about 10 to about 50 basepairs may be needed.

In a more specific embodiment, the primer sequences used in Example 2 below for the amplification of the single KCNQ4 exons, and presented as SEQ ID NOS: 3–32, may be used for the screening of mutations.

The screening may be accomplished by conventional methods, including hybridisation, SSCA analysis, and array technology (DNA chip technology). The hybridisation protocol described above represents a suitable protocol for use in a screening method of the invention.

Therefore, in particular embodiment the invention provides a method for the identification, localisation, isolation or amplification a polynucleotide of the invention, which method a polynucleotide primer of the invention, in particular any one of those presented as SEQ ID NOS: 3–32, is used as a probe. This method may be accomplished using conventional molecular biological techniques, e.g. those used and described in the working examples below.

In a preferred embodiment, the method is used for performing gene amplification using conventional PCR techniques, e.g. as described in the working examples below.

Transgenic Animals

Transgenic animal models provide the means, in vivo, to screen for therapeutic compounds. The establishment of transgenic animals may in particular be helpful for the screening of drugs to fully elucidate the pathophysiology of KCNQ4/DFNA2 deafness. These animals may also be valuable as a model for the frequent condition of presbyacusis that also develops slowly over decades. Since KCNQ4 is expressed also in brain, they may also be helpful in screening for drugs effective in CNS disorders, e.g. epilepsy.

By transgene is meant any piece of polynucleotide which is inserted by artifice into a cell, and thus becomes part of the genome of the organism that develops from that cell. Such a transgene may include a gene which is partly or entirely heterologous (i.e. foreign) to the transgenic organism, or it may represent a gene homologous to an endogenous gene of the organism.

By a transgenic animal is meant any organism holding a cell which includes a polynucleotide sequence which is inserted into that cell by artifice, and which cell becomes part of the transgenic organism which develops from that cell. Such a transgene may be partly or entirely heterologous to the transgenic animal. Although transgenic mice represent a preferred embodiment of the invention, other transgenic mammals including, but not limited to transgenic rodents (e.g. hamsters, guinea pigs, rabbits and rats), and transgenic pigs, cattle, sheep and goats may be created by standard techniques and are included in the invention.

Preferably, the transgene is inserted by artifice into the nuclear genome.

Knock-out and Knock-in Animals

The transgenic knock-out animal models may be developed by homologous recombination of embryonic stem cells with constructs containing genomic sequence from the KCNQ4 gene, that lead to a loss of function of the gene. after insertion into the endogenous gene.

By knock-out mutation is meant an alteration in the polynucleotide sequence that reduces the biological activity of the polypeptide normally encoded therefrom. In order to create a true knock-out model, the biological activity of the expressed polypeptide should be reduced by at least 80% relative to the un-mutated gene. The mutation may in particular be a substitution, an insertion, a deletion, a frame-shift mutation, or a mis-sense mutation. Preferably the mutation is a substitution, an insertion or a deletion.

To further assess the role of KCNQ4 at an organism level, the generation of an animal, preferably a mouse, lacking the intact KCNQ4 gene, or bearing a mutated KCNQ4 gene, is desired.

A replacement-type targeting vector, which may be used to create a knock-out model, may be constructed using an isogenic genomic clone, e.g. from a mouse strain such as 129/Sv (Stratagene Inc., La Jolla, Calif.). The targeting vector may be introduced into a suitably-derived line of embryonic stem (ES) cells by electroporation to generate ES cell lines that carry a profoundly truncated form of the KCNQ4 gene. The targeted cell lines may then be injected into a mouse blastula stage embryo to generate chimeric founder mice. Heterozygous offspring may be interbred to homozygosity.

As the slowly progressive hearing loss observed in DFNA2 may require the expression from one allele of a dominant negative mutant, it may also be desired to create a knock-in animal in which the wild-type KCNQ4 gene is replaced by this mutated gene.

Animal models for over-expression may be generated by integrating one or more polynucleotide sequence of the invention into the genome according to standard techniques.

The procedures disclosed herein involving the molecular manipulation of nucleic acids are known to those skilled in the art, and are described by e.g. Fredrick M A et al. [Fredrick M A et al.: *Short Protocols in Molecular Biology;* John Wiley and Sons, 1995] and Sambrook et al. [Sambrook et al.: *Molecular Cloning: A Laboratory Manual;* 2. Ed., Cold Spring Harbor Lab.; Cold Spring Harbor, N.Y. 1989], and in Alexandra L J (Ed.): *Gene Targeting: A practical approach;* Oxford University Press (Oxford, New York, Tokyo), 1993.

BRIEF DESCRIPTION OF THE DRAWINGS

The present invention is further illustrated by reference to the accompanying drawing, in which.

Figure 1A:
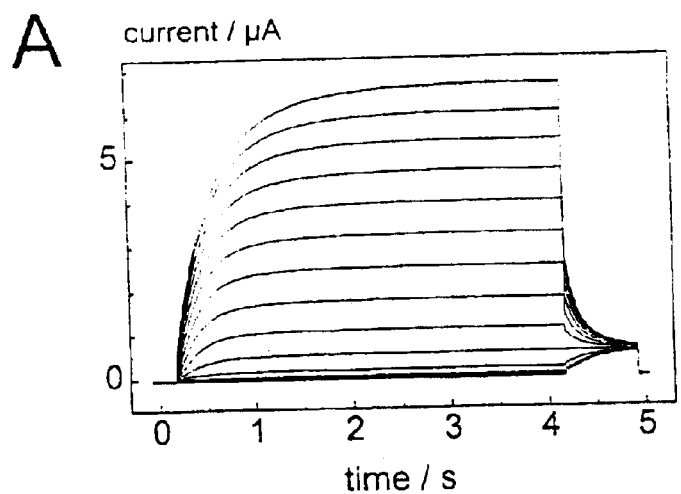
FIG. 1A: Two-electrode voltage-clamp current traces from a Xenopus oocyte injected with KCNQ4 cRNA. Starting from a holding potential of −60 mV cells were clamped for 4 seconds to voltages between −80 . . . +60 mV in +10 mV steps, followed by a constant test pulse to −30 mV.
Figure 1B:
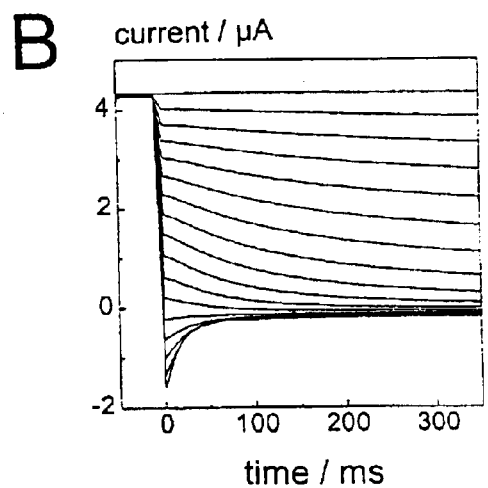
FIG. 1B: Current traces showing the inactivation behaviour of KCNQ4 at different voltages. After an activating voltage pulse at +40 mV of 3.5 seconds duration the cell was clamped to voltages between +40 . . . −120 mV in −10 mV steps.
Figure 1C:
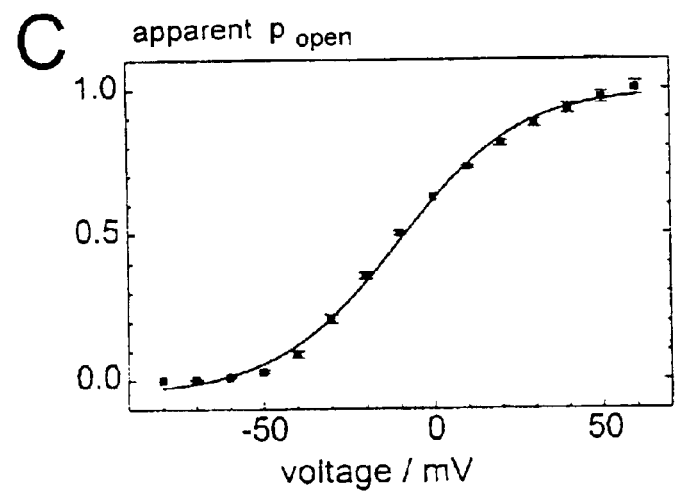
FIG. 1C: Apparent open-probability ($p_{open}$) as a function of voltage determined from tail current analysis of currents as in (A). Half-maximal $p_{open}$ is archived at (−10.0±1.2) mV, and the apparent gating charge is 1.4±0.1, as obtained from a fit of a Boltzmann-function to the data (n=14 from 2 oocyte batches, ±S.E.M.)
Figure 1D:
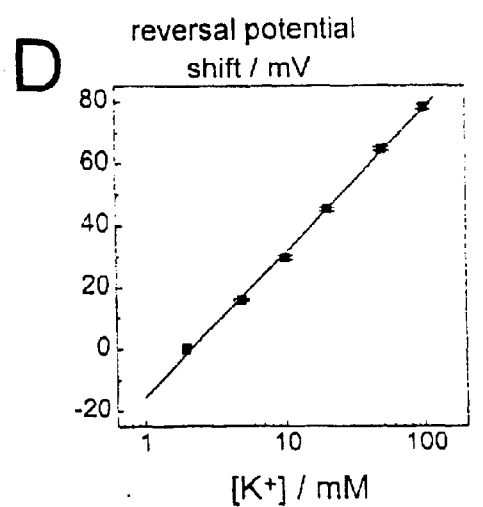
FIG. 1D: Shift of the reversal potential with the extracellular $K^+$-concentration with ND98 as reference solution. Total mono-valent cation concentration was 100 mM and the stated $K^+$-concentration was obtained by mixing solutions ND100 and KD100. The reversal potential shift of 46.7±0.9 mV per decade indicates a channel selective for $K^+$ (n=18 from 3 oocyte batches, ±S.E.M.). Substitution of external K$^+$ with other cations yielded the following permeability ratios: $P_K/P_{Na}$=52.3±4.4, $P_K/P_{Cs}$=7.8±0.7, and $P_K/P_{Rb}$=0.94±0.03 (permeability sequence: Rb$^+$~K$^+$>Cs$^+$>>Na$^+$, n=15 from 3 oocyte batches, ±S.E.M.)
Figure 1E:
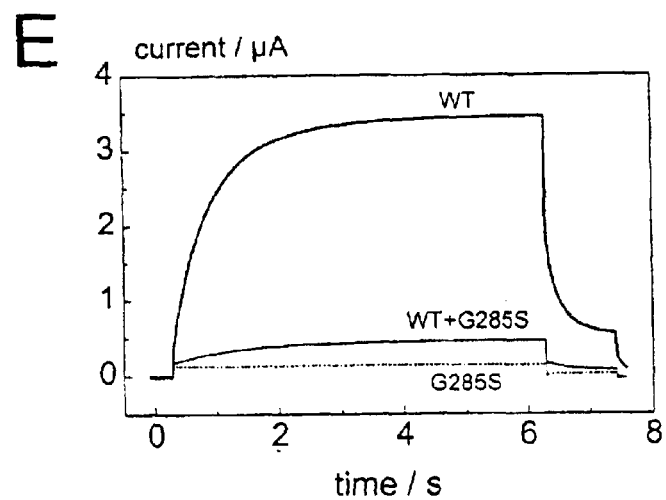
FIG. 1 shows the electrophysiological properties of KCNQ4 currents.
Figure 1F:
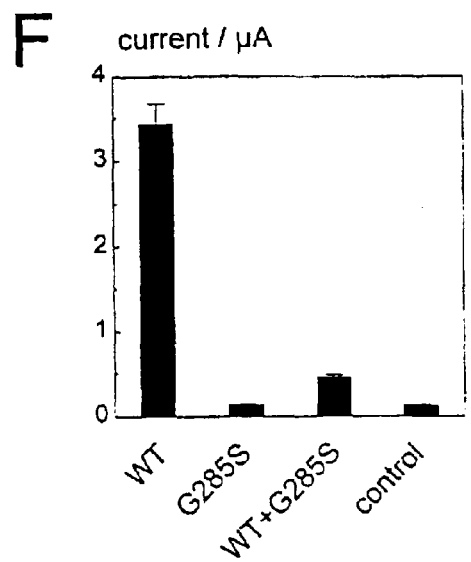
Figure 2A:
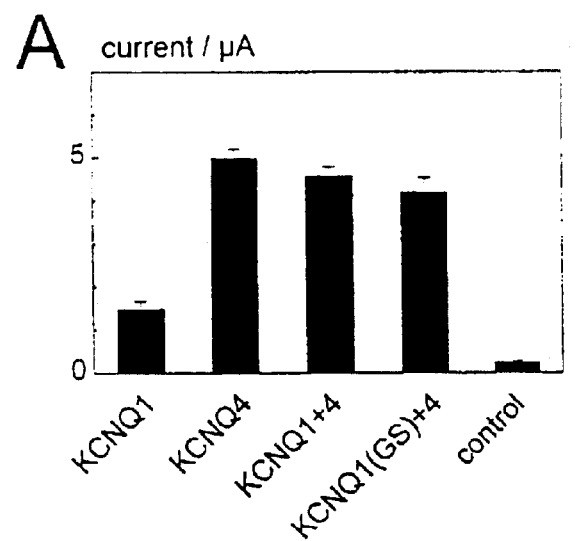
Figure 2B:
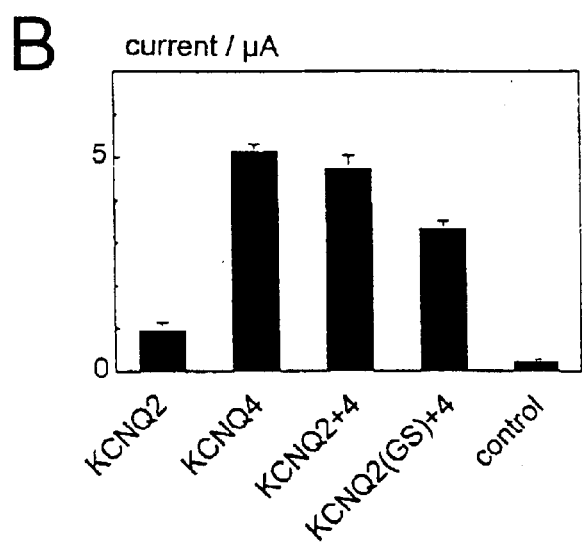
Figure 2C:
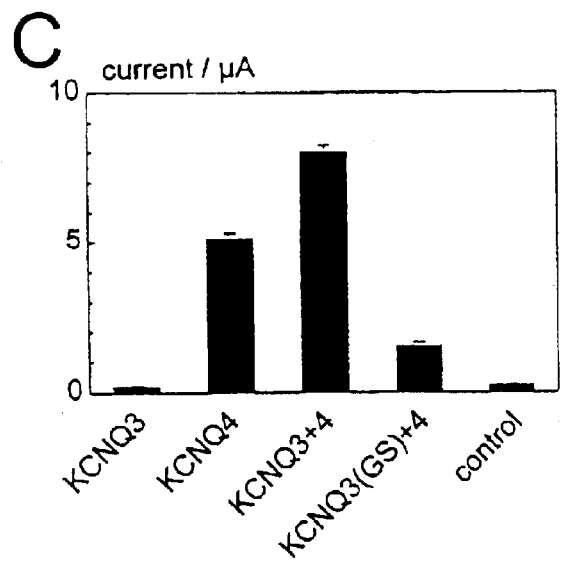

FIG. 1E: Current traces of WT KCNQ4 (thick solid line), a 1:1 co-injection of WT KCNQ4 and KCNQ4$_{G285S}$ mutant (thin solid line) and KCNQ4$_{G285S}$ mutant (dotted line). KCNQ4$_{G285S}$ currents were indistinguishable from water-injected control oocytes. From a holding potential at −60 mV the cells were voltage-clamped for 6 seconds at +40 mV, followed by a −30 mV step;

FIG. 1F: Mean currents, measured after clamping oocytes for 4 seconds at +40 mV, averaged from several experiments as in (1E) (n=20 . . . 35, 4 oocyte batches, ±S.E.M.); and FIG. 2A shows KCNQ4 co-expressed with KCNQ1;

FIG. 2B shows KCNQ4 co-expressed with KCNQ2;

FIG. 2C shows KCNQ4 co-expressed with KCNQ3;

FIG. 2D shows derived dominant negative mutants (KCNQ1$_{G219S}$, KCNQ2$_{G279S}$, KCNQ3$_{G318S}$) (n=10 . . . 31, 3 oocyte batches, ±S.E.) Representative currents from experiments as in (C) showing altered activation kinetics for the co-injection of KCNQ4 with KCNQ3 or KCNQ3$_{G318S}$, respectively. From a holding potential at −60 mV the voltage was clamped for 4 s at +40 mV, followed by a step to −30 mV. Time constants and amplitudes obtained from two-exponential fits were KCNQ4; $t_1$=360 ms, $A_1$=4.9 μA, $t_2$=1700 ms, $A_2$=−0.34 μA; KCNQ3+KCNQ4; $t_1$=120 ms, $A_1$=−6.3 μA, $t_2$=560 ms, $A_2$=−1.3 μA;

FIG. 2E: Apparent $p_{open}$ as a function of voltage for currents from oocytes co-injected with KCNQ4 and KCNQ3 cRNA, determined from tail current analysis (squares, thick solid curve). Half-maximal $p_{open}$ is achieved at $V_{0.5}$=(−19.1±2.0) mV, and the apparent gating charge is 1.5±0.2 (n=23 from 3 oocyte batches, ±S.E.M.), as obtained from a fit of a Boltzmann-function to the data. The $p_{open}$ curve for KCNQ4 is also shown for reference (circles, thin solid curve);

FIG. 2F: Current traces recorded from an oocyte co-injected with KCNQ3 and KCNQ4 cRNA with typical M-current voltage-protocol. Starting from a holding potential at −30 mV the cell was progressively hyperpolarized for 1 s to voltages between −30 and −90 mV in −10 mV steps;

FIG. 2G: Differential effects of 200 μM Linopirdine on KCNQ4 (n=10, ±S.E.M.) and KCNQ3+KCNQ4 (n=6, ±S.E.M.). Currents were measured at +40 mV and % current remaining with Linopirdine is shown. Upon addition of Linopirdine steady-state inhibition was reached after ~1 min for KCNQ4 currents, and after ~3 min for KCNQ3+KCNQ4 currents.

EXAMPLES

The invention is further illustrated with reference to the following examples which are not intended to be in any way limiting to the scope of the invention as claimed.

Example 1

Cloning and Characterisation of KCNQ4 cDNA

Using a KCNQ3 potassium channel partial cDNA as a probe, a human retina cDNA λ phage library (Clontech, #HL1132a) was screened, and a ≈1 kb cDNA encoding a protein fragment homologous to KCNQ potassium channels was isolated. It was distinct from the known members KCNQ1 (KvLQT1), KCNQ2 and KCNQ3. We named the novel gene KCNQ4. Overlapping cDNA's containing the entire open reading frame were obtained by re-screening the cDNA library and by extending the 5' end in RACE (rapid amplification of cDNA ends) experiments using a Marathon kit (Clontech) with human skeletal muscle cDNA. A complete cDNA was assembled and cloned into the oocyte expression vector PTLN [Lorenz C, Pusch M & Jentsch T J: Heteromultimeric CLC chloride channels with novel properties; Proc. Natl. Acad. Sci. USA 1996 93 13362–13366].

The cDNA encodes a polypeptide of 695 amino acids with a predicted mass of 77 kDa (SEQ ID NO: 2). Its overall amino-acid identity to KCNQ1, KCNQ2, and KCNQ3 is 38%, 44%, and 37%, respectively. Together with these proteins it forms a distinct branch of the superfamily of voltage-gated potassium channels. As a typical member of this gene family, KCNQ4 has 6 predicted transmembrane domains and a P-loop between transmembrane domains S5 and S6. In potassium channels, which are tetramers of identical or homologous subunits, four of these highly conserved P-loops combine to form the ion-selective pore. As other KCNQ channels, KCNQ4 has a long predicted cytoplasmic carboxy terminus that accounts for about half of the protein. A conserved region present in the carboxy termini of KCNQ1, -2, and -3 is also present in KCNQ4 (roughly represented by exon 12).

The sequence of KCNQ4 predicts several potential sites for phosphorylation by protein kinase C. In contrast to KCNQ1 and KCNQ2, however, it lacks an amino terminal consensus site for cAMP-dependent phosphorylation.

A human multiple tissue Northern blot (Clontech, #7760-1) was probed with a 749 bp EcoRI/PmlI cDNA fragment of KCNQ4. The fragment was labelled with $^{32}$P using the Rediprime labelling kit (Amersham). Hybridisation was performed in ExpressHyb solution according to the instructions of the manufacturer (Clontech). The filter was then exposed to Kodak BioMax film for 4 days.

Northern analysis of KCNQ4 expression in human tissues revealed faint bands of ≈5 kb in heart, brain and skeletal muscle. In some tissues, there was also a larger band. Upon longer exposure, weaker ≈5 kb bands were also detected in other tissues including kidney and pancreas.

Example 2

Genomic Structure and Chromosomal Mapping to the DFNA2 Locus

A PAC was isolated that contains the entire KCNQ4 coding region. The genomic structure of the KCNQ4 gene was established (SEQ ID NO: 1).

The genomic structure was established by a PCR approach from genomic DNA. Individual KCNQ4 exons and adjacent short intronic sequences were amplified by standard PCR techniques from human genomic DNA using intronic oligonucleotide primers.

For amplification, the following intronic primer pairs were used (all primers in 5'→3' direction; in brackets the size of the PCR product):

1a (SEQ ID NO: 3): catgcgtctctgagcgccccgagc 1r (SEQ ID NO: 4): aggccaggcttgcgcggggaaacg   (544)

-continued 2a (SEQ ID NO: 5): cagcacagagctgtaactccagg 2r (SEQ ID NO. 6): aagctgctctctgagccatgg (500)

3a (SEQ ID NO: 7): gctgggtccgcgctgtgacc 3r (SEQ ID NO: 8): ggtctccagggtcagagtcg (292)

4a (SEQ ID NO: 9): tccgggtccgtgcgcggggta 4r (SEQ ID NO: 10): gagacagccctctgacctcg (328)

5a (SEQ ID NO: 11): atcccttccccgtgtggaagc 5r (SEQ ID NO: 12): agtcacgatgggcagacctcg (286)

6a (SEQ ID NO: 13): cctcatgatcaggctcctacc 6r (SEQ ID NO: 14): atgtgtgacaggggtgagc (270)

7a (SEQ ID NO: 15): aaggatggggacacccttgc 7r (SEQ ID NO: 16): acacagggttgacacacc (244)

8a (SEQ ID NO: 17): gctctgggtaacccacaactg 8r (SEQ ID NO: 18): gctccctgggagccatcacc (316)

9a (SEQ ID NO: 19): tgagctcaggagctctgtgc 9r (SEQ ID NO: 20): acccacgaagtggctgaaggc (346)

10a (SEQ ID NO: 21): gtcctaagtcagctttgtcc 10r (SEQ ID NO: 22): cctcagccggccctcgatcg (347)

11a (SEQ ID NO: 23): cactctactggtggtttggc 11r (SEQ ID NO: 24): ctcctgacctcaagtgatcc (281)

12a (SEQ ID NO: 25): gatagcaaagagatggagagg 12r (SEQ ID NO: 26): aactcagctgcagcagtgagc (328)

13a (SEQ ID NO: 27): gtgccttctccttcatcaggc 13r (SEQ ID NO: 28): aacgcatcctccccatgtca (297)

14a (SEQ ID NO: 29): tttgtgcttcccagataagc 14r (SEQ ID NO: 30): cgtgagggagtgagttcaagtacg (445)

Sequences of exons and adjacent introns are deposited in GenBank (Accession Numbers AF105203-AF105216).

To screen unlinked pedigrees with autosomal dominant deafness we amplified only exons 4 through 7 that code for the pore and adjacent transmembrane domains as these may have the highest likelihood to harbour mutations. After amplification and agarose gel purification, PCR products were directly sequenced using the amplification primers and an ABI377 automated DNA sequencer.

The highly conserved transmembrane block S1-S6 was found to be encoded by 6 exons (exons 2 to 7) having the same limits as in KCNQ2 and KCNQ3. In KCNQ1 an additional intron interrupts the sequence encoding domain S4. The exon-intron structures of KCNQ genes diverge most in the poorly conserved carboxy-termini of these proteins.

Using hybridisation to human chromosomes, KCNQ4 was mapped to 1p34.

A PAC containing the coding sequence of KCNQ4 was isolated using intronic KCNQ4 oligonucleotide primers and PCR. It was used to localise KCNQ4 to 1p34 using FISH (Genome Systems). KCNQ4 was then mapped on the Whitehead Contig WC1.10 using several of the intronic primers given above and published STS markers by PCR amplification from individual YAC clones.

Several diseases have been mapped to this region. This includes DFNA2, a locus for dominant progressive hearing loss. Due to the critical role of $K^+$ homeostasis in auditory mechano transduction, we considered KCNQ4 as an excellent candidate gene for DFNA2. The DFNA2 locus has been mapped between markers D1S255 and D1S193. We therefore refined the localisation of KCNQ4 in comparison to published physical and genetic maps using a YAC (yeast artificial chromosome) contig of this region. KCNQ4 was present on CEPH YAC clone 914c3, a result which places this gene within the DFNA2 region.

Example 3

Expression of KCNQ Genes in the Inner Ear

The expression of KCNQ4, as well as of other KCNQ genes, was studied by semi-quantitative RT-PCR on mouse cochlear RNA.

RT-PCR Analysis of Mouse KCNQ mRNA Expression

Approximately 2 μg of mouse total brain RNA and mouse cochlear and vestibular RNA were reverse transcribed using the SuperScript™ II (Gibco BRL) reverse transcriptase.

1 μl (resp. 1 μl of a 1:10 dilution) of cDNA was amplified for 30 cycles (96° C. for 30 sec, 61° C. for 30 sec, and 68° C. for 45 sec) using a 2400 Thermocycler System (Perkin Elmer). Each 50 μl reaction contained 2.5 U polymerase (Expand™ Long Template PCR System, Boehringer Mannheim) and 5% DMSO.

KCNQ1 primers were based on the mouse cDNA sequence (GenBank Accession # U70068):

MK1a 5'-aaggctggatcagtccattgg-3' (SEQ ID NO:36)

and

MK1r 5'-aggtgggcaggctgttgctgg-3' (280 bp) (SEQ ID NO:37)

As no mouse KCNQ2 sequence was available, we chose sequences conserved between human (Y15065) and rat (AF087453) KCNQ2:

MK2a 5'-gccacggcacctcccccgtgg-3' (SEQ ID NO:38);

and

MK2r 5'-ccctctgcaatgtagggcctgac-3' (331 bp) (SEQ ID NO:39)

KCNQ3 primers were derived from a mouse EST (AA386747):

MK3a 5'-ccaaggaatgaaccatatgtagcc-3' (SEQ ID NO:40);

and

MK3r 5'-cagaagagtcaagatgggcaggac-3' (461 bp) (SEQ ID NO:41)

Mouse KCNQ4 primers were:

(SEQ ID NO: 31): MK4a 5'-agtacctgatggagcgccctctcg-3';

and (SEQ ID NO: 32): MK4r 5'-tcatccaccgtaagctcacactgg-3' (366 bp)

Amplification products were verified by direct sequencing.

These results were compared with those obtained with vestibular and brain RNA.

KCNQ1, KCNQ3 and KCNQ4 messages can be detected in the cochlea, and additional PCR cycles revealed a weak KCNQ2 expression as well. At this high amplification, KCNQ1 was also detected in brain. KCNQ1 and KCNQ4 appear to have the highest cochlear expression. KCNQ1 expression is higher in the cochlea than in brain (which was negative by Northern analysis). The reverse is true for KCNQ2 and KCNQ3, both of which are broadly expressed in brain. KCNQ4 expression is significant in both of these tissues.

In situ Hybridisation of Mouse Cochlea

In situ hybridisation's were performed on cochlea sections from mice at postnatal day P12 with a KCNQ4 antisense probe.

A mouse KCNQ4 cDNA corresponding to bp 618 to 1602 of the human KCNQ4 ORF was cloned into pBluescript. Sense and antisense probes were transcribed using T3 and 17 RNA polymerases after appropriate linearization. After DNAse digestion, the probes were ethanol precipitated twice with 0.4 M LiCl. They were labelled with digoxigenin-11-UTP as described previously (Schaeren-Wiemers and Gerfin-Moser, 1993).

Mouse inner ears were fixed for 1 hour at 4° C. in 4% paraformaldehyde in PBS. After three rinses in PBS, they were immersed in 20% sucrose overnight at 4° C. Cryostat sections (10–14 µm) were post-fixed and rinsed in PBS. Following pre-hybridisation at room temperature for at least 3 hours, they were hybridised overnight at 58° C. in a humid chamber. Sections were then washed and incubated with sheep antidigoxigenin antibody coupled to alkaline phosphatase. Staining by NBT/BCIP (Boehringer Mannheim) was done for 2 hours at 37° C. and overnight at RT. Sections were then mounted in Aquatex (Merck, USA).

Sensory outer hair cells were strongly labelled. By contrast, the inner hair cells appeared negative. The stria vascularis, the site of KCNQ1 expression, was negative as well. Control hybridisation with a KCNQ4 sense probe revealed that the staining of outer hair cells was specific.

Autosomal Dominant Deafness

These results indicated that KCNQ4 was an excellent candidate gene for autosomal dominant deafness. As we did not have access to the published pedigrees that were linked to the DFNA2 locus, we screened 45 families with autosomal dominant deafness without previous linkage analysis. In most of these families, the hearing loss had been diagnosed before adulthood, i.e. before the age of onset reported for most of the DFNA forms, including DFNA2.

Mutation screening was limited to exons 4 to 7 that encode the pore region and adjacent transmembrane domains. A KCNQ4 mutation was found in a French family with profound hearing loss. Its clinical features include progressive hearing loss that is more prominent with higher frequencies, tinnitus in one patient, and no indication for vestibular defects nor gross morphological changes in the inner ear. A mis-sense mutation (cf. SEQ ID NO: 1; The mutation G935A at the nucleotide level giving rise to the variant G285S at the amino acid level) was present in exon 6 in a heterozygous state. Using an AluI restriction site (AGCT) introduced by this mutation, it was shown that it co-segregated with all affected members in the pedigree. This mutation was not found on 150 control Caucasian chromosomes.

The G285S mutation affects the first glycine in the GYG signature sequence of potassium channel pores. This glycine is highly conserved across different classes of potassium channels in all species. The crystal structure of the *Streptomyces lividans* potassium channel reveals that these three amino acids line the narrowest part of the ion-conductive pore. Mutations in these amino-acids disrupt the selectivity filter and in most cases lead to a loss of channel function. Interestingly, an identical change in amino acids at the equivalent position was found in the KCNQ1 gene of a patient with the dominant long QT syndrome. It disrupted channel activity and exerted a dominant negative effect on co-expressed WT KCNQ1 channels. These mutations also have dominant negative effects when inserted into KCNQ2 and KCNQ3. This is strong evidence that the progressive hearing loss in this family is due to the KCNQ4/G285S mutation.

Example 4

Functional Expression of KCNQ4 Potassium Channel Subunits

KCNQ4 was expressed in Xenopus oocytes and its activity was investigated by two-electrode voltage clamping.

After linearization of the KCNQ4-containing PTLN vector with HpaI, capped cRNA was transcribed in vitro using the mMessage mMachine cRNA synthesis kit (Ambion). Usually 5–15 ng of cRNA were injected into Xenopus oocytes previously isolated by manual defolliculation and short collagenase treatment. In co-expression experiments cRNAs were injected at a 1:1 ratio. Oocytes were kept at 17° C. in modified Barth's solution (90 mM NaCl, 1 mM KCl, 0.41 mM $CaCl_2$, 0.33 mM $Ca(NO_3)_2$, 0.82 mM $MgSO_4$, 10 mM HEPES, 100 U penicillin-100 µg streptomycin/ml, pH 7.6).

Standard two-electrode voltage-clamp measurements were performed at room temperature 24 days after injection using a Turbotec 05 amplifier (npi instruments, Tamm, Germany) and pClamp 5.5 software (Axon Instruments). Currents were usually recorded in. ND98 solution (see Table 2). Solutions for $Na^+/K^+$ replacement experiments were prepared from an appropriate mixture of solution KD100 (100 mM KCl) and ND100 (100 mM NaCl) to yield the stated concentrations of $Na^+$ and $K^+$. Linopirdine (RBI, Natick, Mass.) was prepared as a 100 mM stock solution in DMSO and added to a final concentration of 200 µM to ND98.

TABLE 2

| Solution contents (concentrations in mM) | | | | |
| --- | --- | --- | --- | --- |
| ND98 | ND 100 | KD100 | Rb100 | Cs100 |
| 98 NaCl | 100 NaCl | 100 KCl | 100 RbCl | 100 CsCl |
| 2 KCl | | | | |
| 0.2 $CaCl_2$ | 0.2 $CaCl_2$ | 0.2 $CaCl_2$ | 0.2 $CaCl_2$ | 0.2 $CaCl_2$ |
| 2.8 $MgCl_2$ | 2.8 $MgCl_2$ | 2.8 $MgCl_2$ | 2.8 $MgCl_2$ | 2.8 $MgCl_2$ |
| 5 mM HEPES pH 7.4 | | | | |

Reversal potentials were determined from tail currents after a 2 s depolarising pulse to +60 mV and corrected for liquid junction potentials that were determined experimentally. The permeability ratios were calculated according to $P_K/P_X = \exp(-F \cdot V_{rev}/R \cdot T)$.

To determine the voltage dependence of apparent open probability, oocytes were clamped for 4 s to values between −80 mV to +50 mV in 10 mV steps, followed by a constant −30 mV test pulse. Tail currents extrapolated to t=0 were obtained from a mono-exponential fit, normalised to the value at 0 mV and used for the analysis of apparent $p_{open}$. Data analysis used PClamp6 and Microcal Origin 5.0.

Similar to KCNQ1, KCNQ2 and KCNQ3, also KCNQ4 yielded currents that activated upon depolarisation (FIG. 1A). Compared to those other KCNQ channels, however, current activation was slower and occurred with a time constant in the order of 600 ms at +40 mV (KCNQ2/KCNQ3 channels have a corresponding time constant of ≈300 ms). This time constant was very sensitive to changes in temperature. Deactivation of currents at physiological resting potentials (≈-70 mV) was considerably faster (FIG. 1B). Similar to KCNQ2, macroscopic currents often showed some inward rectification at positive potentials. When oocytes were depolarised to +60 mV for 10 sec or more, an apparent slow inactivation of currents was observed that resembled the one described for KCNQ3. Currents began to activate at about -40 mV, with half-maximal activation at -10 mV (FIG. 2C). Ion substitution experiments showed that the channel is highly selective for potassium (FIG. 1D). It has a $K^+≈Rb^+>Cs^+>Na^+$ permeability sequence. KCNQ4 currents were inhibited by more than 80% by 5 mM $Ba^{++}$.

We next examined the effect of the G285S mutation found in the affected family (FIGS. 1E and 1F). The mutant channel did not yield any detectable currents in the Xenopus oocyte expression system. $KCNQ4_{G285S}$ was then injected at a 1:1 ratio with WT KCNQ4 to mimic the situation in a heterozygous DFNA2 patient. This reduced currents by about 90%, indicating a strong dominant negative effect of the mutant. The degree of current reduction is compatible with the notion that the incorporation of one mutant subunit suffices to abolish the function of the tetrameric channel complex. The channels present in co-injected oocytes still showed a strong preference of potassium over sodium or calcium. This implies that the deafness is due to a quantitative loss of KCNQ4 potassium currents rather than to an influx of sodium or calcium.

KCNQ1 assembles with minK (IsK) to form channels that yield larger currents and activate much slower. We therefore tested by co-expression whether minK affects KCNQ4 as well. At concentrations (1 ng minK cRNA per oocyte) leading to drastic changes in KCNQ1 currents in parallel experiments, there was no significant change in KCNQ4 currents.

Different KCNQ subunits can form heteromeric channels. Co-expression of KCNQ2 with KCNQ3, but not with KCNQ1, gave currents that were about tenfold larger than those from homomeric channels. Since also KCNQ1 and KCNQ3 (and to a lesser degree also KCNQ2) are expressed in the cochlea, we investigated whether these proteins interact functionally. Oocytes co-injected (at the same total cRNA concentration) with KCNQ1 and KCNQ4 cRNAs yielded currents that seemed not different from a linear superposition of currents from the respective homomeric channels (FIG. 2A), and the same was true for oocytes co-expressing KCNQ2 and KCNQ4 (FIG. 2B). In addition, a dominant negative KCNQ1 mutant did not suppress KCNQ4 currents (FIG. 2A), and the same was true for the equivalent KCNQ2 mutant (FIG. 2B).

By contrast, co-expression of KCNQ3 with KCNQ4 yielded currents that were significantly larger than could be explained by a superposition of currents from the respective homomeric channels (FIGS. 2C and 2D). Further, KCNQ4 currents were markedly suppressed by co-expressing a dominant negative KCNQ3 mutant (FIG. 2C). Importantly, currents from co-injected oocytes activated faster than KCNQ4 currents (FIG. 2D), and there was a ≈10 mV shift of the open probability towards negative voltages (FIG. 2E). Compared to KCNQ2/KCNQ3 channels, which may underlie the M-current, KCNQ3/KCNQ4 heteromers open at slightly more positive voltages. To compare KCNQ3/KCNQ4 channels to M-channels, we used the typical voltage-protocol employed for these channels and found currents superficially resembling M-currents (FIG. 2F). Linopirdine, a potent and rather specific inhibitor for M-currents, nearly completely inhibits KCNQ2/KCNQ3 channels at a concentration of 200 μM. This concentration of Linopirdine inhibited KCNQ4 by about 30%, while a significantly larger inhibition (≈75%) was observed with KCNQ3/KCNQ4 co-expression (FIG. 2G).

What is claimed is:

1. An isolated polynucleotide having a nucleic acid sequence which is capable of hybridizing under high stringency conditions with the polynucleotide sequence of SEQ ID NO: 1, or its complementary strand, wherein said hybridizing occurs in a solution of 5×SSC, 5×Denhardt's solution, 0.5% SDS and 100 µg/ml of denatured sonicated salmon sperm DNA for 12 hours at approximately 45° C. followed by washing twice for 30 minutes in 2×SSC, 0.5% SDS at a temperature of at least 65° C., wherein said polynucleotide encodes an amino acid sequence which is a sub-unit of a KCNQ4 potassium channel and which, when joined with other subunits makes up a functional potassium channel.

2. The isolated polynucleotide according to claim 1, wherein said isolated polynucleotide is at least 90% homologous to the polynucleotide sequence of as SEQ ID NO: 1.

3. The isolated polynucleotide according claim 1, wherein said isolated polynucleotide is a cloned polynucleotide.

4. The isolated polynucleotide according to claim 3, wherein the polynucleotide is cloned from, or produced from a cDNA library.

5. The isolated polynucleotide according to claim 1, comprising the polynucleotide sequence presented as SEQ ID NO: 1.

6. The isolated polynucleotide according to claim 1, comprising the polynucleotide sequence of SEQ ID NO: 1, wherein said sequence includes a mutation G935A.

7. The isolated polynucleotide according to claim 1, encoding a KCNQ4 potassium channel subunit comprising the amino acid sequence of SEQ ID NO: 2.

8. The isolated polynucleotide according to claim 1, encoding a variant KCNQ4/G285S when said polynucleotide is numbered according to SEQ ID NO: 1.

9. An isolated cell genetically manipulated by the incorporation of a heterologous polynucleotide according to claim 1.

10. The cell according to claim 9, genetically manipulated by the incorporation of a KCNQ4 channel subunit comprising the amino acid sequence of SEQ ID NO: 2.

11. The cell according to claim 9, genetically manipulated by the incorporation of the variant KCNQ4/G285S when numbered according to SEQ ID NO: 1.

12. The cell according to claim 9, wherein said cell co-expresses one or more KCNQ channel subunits.

13. The cell according to claim 12, wherein said cell co-expresses KCNQ4 and KCNQ1 channel subunits, KCNQ4 and KCNQ2 channel subunits, KCNQ4 and KCNQ3 channel subunits, KCNQ4 and KCNQ1 and KCNQ2 channel subunits, KCNQ4 and KCNQ1 and KCNQ3 channel subunits, KCNQ4 and KCNQ2 and KCNQ3 channel subunits, or KCNQ4 and KCNQ1 and KCNQ2 and KCNQ3 channel subunits.

14. The cell according to claim 12, wherein said cell co-expresses KCNQ3 and KCNQ4 channel subunits.

15. The cell according to claim 9, wherein said cell is a human embryonic kidney (HEK) cell, a HEK 293 cell, a BHK21 cell, a Chinese hamster ovary (CHO) cell, a *Xenopus laevis* oocyte (XLO) cell, a COS cell, or any other cell line that expresses KCNQ potassium channels.

16. A method for obtaining a substantially homogeneous source of a human potassium channel comprising a KCNQ4 subunit, comprising the steps of culturing a cellular host having incorporated expressly therein a polynucleotide according to claim 1, recovering the cultured cells and obtaining said human KCNQ4 subunit.

17. The method of claim 16, further comprising the step of obtaining a membrane preparation from the cultured cells, and wherein said membrane preparation comprises said KCNQ4 subunit encoded by said polynucleotide sequence.

18. A cell line genetically manipulated by the incorporation of a heterologous polynucleotide according to claim 1, wherein the polypeptide encoded by said heterologous polynucleotide in incorporated into the cell membrane.

19. The isolated polynucleotide according to claim 2, wherein said isolated polynucleotide is at least 95% homologous to the polynucleotide sequence of SEQ ID NO:1.

20. The isolated polynucleotide according to claim 1, wherein maid nucleic acid sequences capable of hybridizing under high stringency conditions with the polynucleotide sequence of SEQ ID NO:1 or its complimentary strand, wherein said hybridizing occurs in a solution of 5×SSC, 5×Denhardt's solution, 0.5% SDS and 100 µg/ml of denatured sonicated salmon sperm DNA for 12 hours at approximately 45° C. followed by washing twice for 30 minutes in 2×SSC, 0.5% SDS at a temperature of at least 70° C.

21. The isolated cell of claim 9, wherein the polypeptide encoded by said heterologous polynucleotide is incorporated into the cell membrane.

22. The membrane preparation according to claim 21, and wherein said membrane preparation comprises the polypeptide sequence of SEQ ID NO: 2.

23. The method of claim 16, further comprising the step of obtaining a membrane preparation from the cultured cells, and wherein said membrane preparation comprises the polypeptide sequence of SEQ ID NO: 2.

24. A membrane preparation derived from a cell according to claim 21, and wherein said membrane preparation comprises said polypeptide encoded by said heterolgous polynucleotide sequence.

* * * * *